US006252242B1

(12) United States Patent
Brunfeld et al.

(10) Patent No.: US 6,252,242 B1
(45) Date of Patent: *Jun. 26, 2001

(54) HIGH SPEED OPTICAL INSPECTION APPARATUS USING GAUSSIAN DISTRIBUTION ANALYSIS AND METHOD THEREFORE

(75) Inventors: Andrei Brunfeld, Bat-Yam; Joseph Shamir, Haifa; Gregory Toker, Jerusalem; Liviu Singher, Haifa; Ilan Laver; Ely Pekel, both of Kefar Saba, all of (IL)

(73) Assignee: Brown & Sharpe Surface Inspection Systems, Inc., North Kingstown, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/985,632

(22) Filed: Dec. 3, 1992

(51) Int. Cl.[7] .................................................. G01H 21/88
(52) U.S. Cl. ................................. 250/559.45; 356/239.1
(58) Field of Search ................................. 250/234–236, 250/562, 563, 571, 572, 559.45, 559.48, 559.49; 356/238, 239, 429–431, 237.1, 237.2, 239.1; 364/507; 209/588

(56) References Cited

U.S. PATENT DOCUMENTS

| | | | | |
|---|---|---|---|---|
| 3,836,261 | * | 9/1974 | Clarke | 250/571 |
| 3,900,265 | * | 8/1975 | Merlen | 356/431 |
| 4,376,583 | * | 3/1983 | Alford et al. | 250/572 |
| 4,505,585 | * | 3/1985 | Yoshikawa et al. | 356/237 |
| 4,924,086 | * | 5/1990 | Wiber | 250/235 |
| 4,954,723 | * | 9/1990 | Takahashi | 250/563 |
| 5,031,112 | * | 7/1991 | Sakai | 364/507 |
| 5,135,308 | * | 8/1992 | Uto et al. | 250/563 |

* cited by examiner

Primary Examiner—Stephone B. Allen
(74) Attorney, Agent, or Firm—Wolf, Greenfield & Sacks, P.C.

(57) ABSTRACT

An optical inspection apparatus operates at high speed at very high resolution for detecting defects in flat, polished media in a production environment. The configuration of the first embodiment is used to inspect transparent disks such as those used as disk platters in hard disk drives. The configuration of the second embodiment is used to inspect reflective disks. The configuration of the third embodiment is used to inspect transparent flat panels such as those commonly used in Liquid Crystal Display (LCD) panels. All embodiments use a laser providing a light beam directed to a polygon scanner, which provides a linear scan of the beam. The unit to be inspected is moved such that its entire surface passes the scan path of the light beam. The light beam, after contacting the unit to be inspected, is directed to a parallel detector array, which detects changes in the nominal Gaussian distribution of the light beam that correspond to defects above a programmable threshold level. This parallel detection method allows the inspection apparatus to identify defects much smaller than the diffraction limits of the optics used, and will accurately identify changes in the light beam caused by defects in the media. An automatic media handler loads untested units into the apparatus and unloads and sorts tested units according to the results of the inspection.

107 Claims, 12 Drawing Sheets

REFLECTIVE DISK INSPECTION SYSTEM

TRANSPARENT DISK INSPECTION SYSTEM

REFLECTIVE DISK INSPECTION SYSTEM

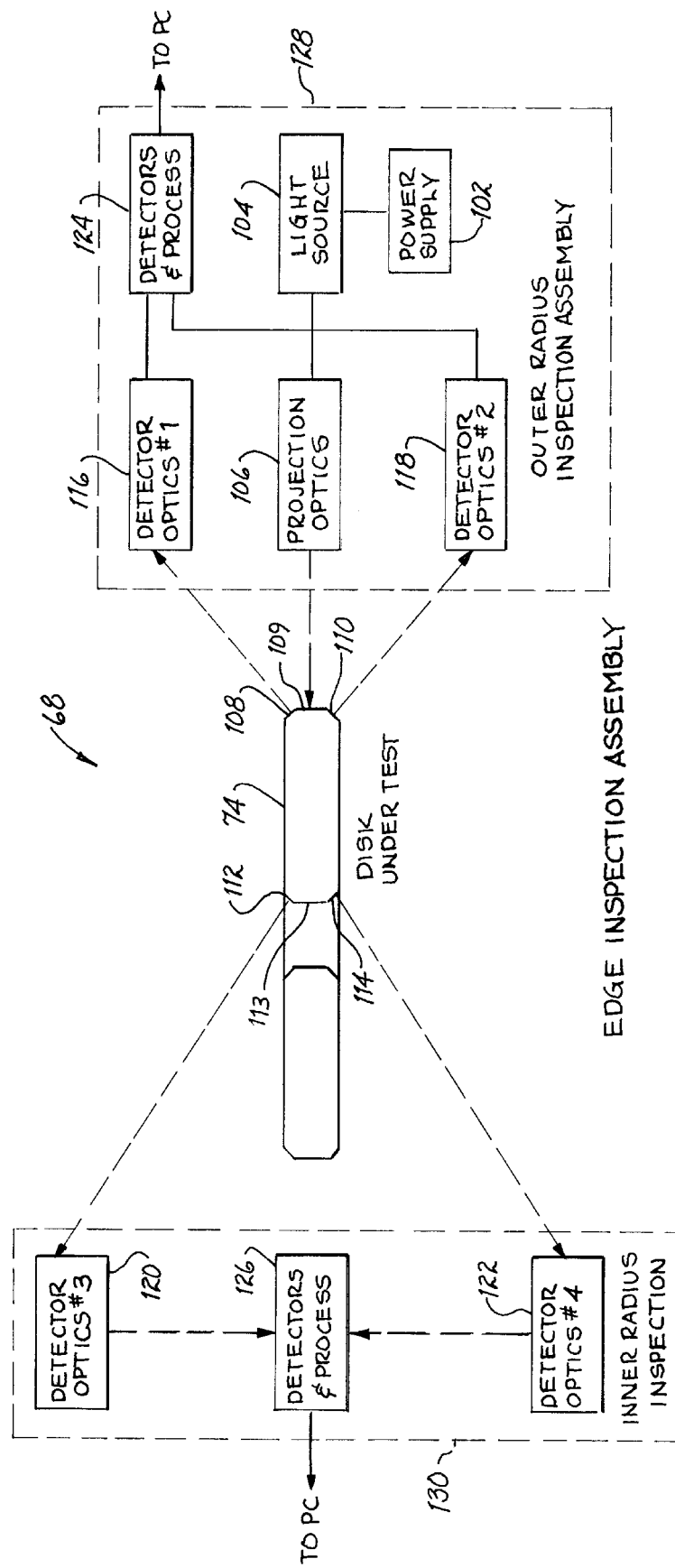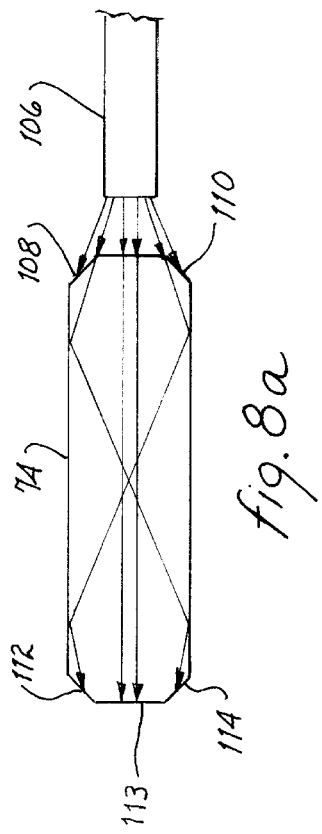
fig. 8
fig. 8a

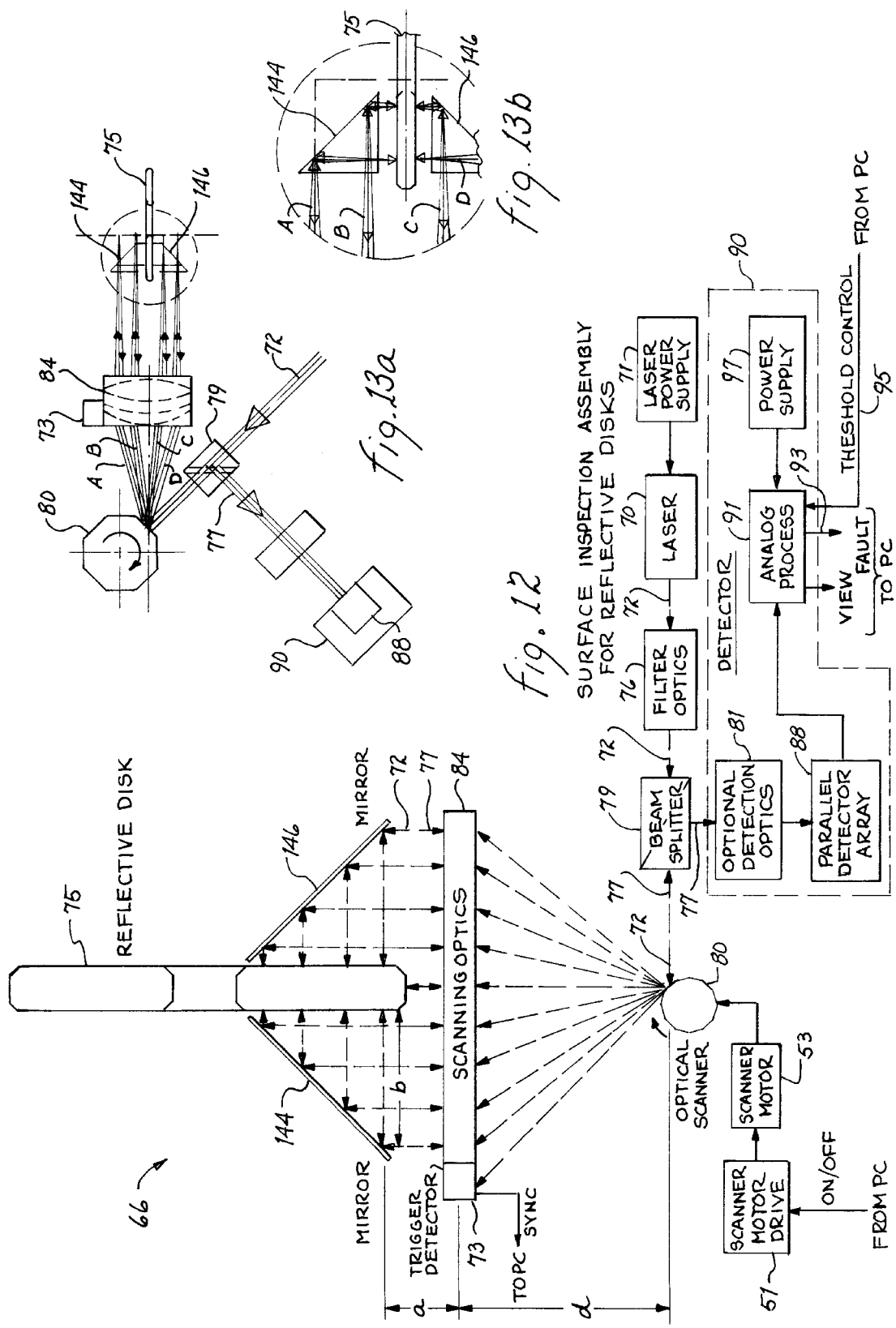

TRANSPARENT FLAT PANEL INSPECTION SYSTEM

PARALLEL DETECTOR ARRAY

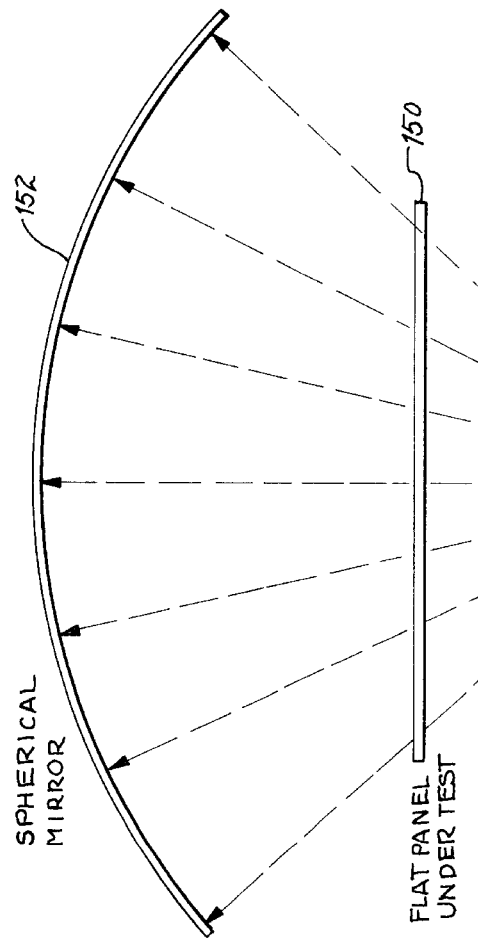

HIGH SPEED OPTICAL INSPECTION APPARATUS USING GAUSSIAN DISTRIBUTION ANALYSIS AND METHOD THEREFORE

RELATED APPLICATIONS

This patent application is related to three other U.S. patent applications entitled: "High Speed Optical Inspection Apparatus for a Transparent Disk and Method Therefor", "High Speed Optical Inspection Apparatus for a Reflective Disk and Method Therefor", and "High Speed Optical Inspection Apparatus for a Transparent Flat Panel and Method Therefor" which are assigned to the same assignee as this patent application and which are filed on the same date as the date of this patent application.

FIELD OF THE INVENTION

This invention generally relates to optical apparatus and methods, and relates, more specifically, to an optical inspection apparatus and method for detecting faults in flat, polished transparent and reflective media, which inspects with high resolution at high speed with automatic handling of the media to allow the apparatus to be used effectively in a production inspection environment. The apparatus of the present invention is well-suited to the inspection of transparent and reflective disks used as platters for hard disk drives, and to the inspection of transparent flat panels such as those commonly used in Liquid Crystal Display (LCD) panels.

DESCRIPTION OF THE PRIOR ART

Disks for hard disk drives require a surface that is flat to a high degree of accuracy, and that is free from defects such as scratches and chips. Likewise, flat panels also have requirements for flatness and absence of defects. Some optical inspection systems have been used with limited success in inspecting media such as disks and flat panels, but do not provide the accuracy or speed that is needed in a production environment.

Dark field microscopes and scatterometers are inspection apparatus well-known in the art. A dark field microscope can somewhat accurately locate surface defects, but takes too long to inspect to be effectively used in a production environment. A scatterometer is faster than a dark field microscope, but has less accuracy (detects fewer defects). Both the dark field microscope and the scatterometer have low detection sensitivity to shallow defects or defects that have a depth less than the wavelength of the light used, which cause a phase shift in the light beam but do not diffuse (scatter) the light in different directions. An interferometer, which is well-known in the art, is suitable to detecting phase shifts, but takes substantial time and effort to set up, limiting its use to laboratory environments.

The inherent limitations of the prior art inspection systems have limited their use in industrial production environments. Indeed, the most common inspection method used in a production environment is a manual, visual inspection by human inspectors, which hold the disk or flat panel in their hands and move it in ambient or special light looking for the presence of scratches, chips and other defects. This inspection method is labor intensive, relatively slow, and subject to human errors such as missed defects which the human eye cannot easily distinguish.

Therefore, there existed a need to provide a high speed optical inspection system and method which has a high sensitivity to defects which can be used to inspect both transparent and reflective media in a production environment. This inspection system includes automatic handling of the media, high speed inspection, and high resolution to detect defects smaller that the spot size of the beam and/or more shallow that the wavelength of light used. The increased speed of this apparatus increases throughput of the production system, and assures that any mistakes or defects introduced by human inspectors is eliminated.

SUMMARY OF THE INVENTION

It is an object of this invention to provide a high-speed optical inspection apparatus and method suitable for production testing of transparent disks.

It is another object of this invention to provide a high speed optical inspection apparatus and method suitable for production testing of reflective disks.

It is a further object of this invention to provide a high speed optical inspection apparatus and method suitable for production testing of transparent flat panels.

It is a still further object of this invention to provide a high speed optical inspection apparatus and method which is computer-controlled using an IBM PC-AT computer or equivalent.

It is still another object of this invention to provide a high speed optical inspection apparatus and method with surface inspection which has a high speed optical scanner to provide linear movement of the beam across the width of the media, and a media actuator to position each portion of the media in the path of the linear movement of the beam, thereby completely inspecting the entire face surface of the media.

It is yet another object of this invention to provide a high speed optical inspection apparatus and method with edge inspection (if required) using a light source and linear Charge-Coupled Device (CCD) cameras which scan the edge of the media as it is moved as needed during surface inspection.

It is still another object of this invention to provide a high speed optical inspection apparatus and method which has an automatic media handler for automatically loading the media into the apparatus and for automatically unloading the media from the apparatus.

It is a still further object of this invention to provide a high speed optical inspection apparatus and method which detects both phase and amplitude changes of the light beam using multiple detectors to sense changes in the nominal Gaussian distribution of the light beam.

It is yet another object of this invention to provide a high speed optical inspection apparatus and method which has a trigger detector within the path of the scanning light beam to provide a signal to synchronize the controlling computer to the scan of the light beam.

According to the present invention, an optical inspection apparatus is provided. This inspection apparatus is controlled by an IBM PC-AT computer or equivalent, and has a typical color monitor, printer and keyboard. An Optical Inspection Assembly is provided which comprises a Surface Inspection Assembly and an Edge Inspection Assembly (if required). The Surface Inspection Assembly nominally comprises a laser light source which transmits a light beam, a high-speed Optical Scanner, Scanning Optics, Detection Optics, and a Parallel Detector Array within a Detector. The computer controls the automatic loading and unloading of the media by sending appropriate control signals to the Automatic Media Handler. The computer also controls the movement of the media across the linear scan of the Optical Scanner within the Surface Inspection Assembly to assure the entire surface of the media is inspected. While the media is being moved, both the Surface Inspection Assembly and the Edge Inspection Assembly (if present) simultaneously perform their respective inspections. Surface defects are detected by changes in the nominal light level or in the two-dimensional Gaussian distribution of the detected light beam as explained in more detail below. Edge defects are detected using cameras to monitor the illuminated edges of the media. Any defect detected that exceeds a programmable threshold is reported to the computer, causing the inspection to fail.

The Optical Scanner causes a linear scan of the light beam across one axis of the media. After contact with the media the light beam goes to a Parallel Detector Array. This array is typically a matrix of photodiodes or Charge-Coupled Devices (CCDs) upon which the light beam is projected. This matrix configuration provides a two dimensional Gaussian response with respect to light intensity (amplitude). Any defect in the media deflects light from the Parallel Detector Array (causing a change in the nominal light level) or shifts its phase (causing a change in the Gaussian distribution), both of which are detected by the processing electronics coupled to the Parallel Detector Array. Thus the processing electronics simply look for changes in the nominal level or distribution of the Gaussian response provided by the Parallel Detector Array in response to a nominal light beam. Any defect that exceeds a programmable threshold value is reported to the computer, which causes the inspection to fail. Note that the Automatic Media Handler sorts the tested media according to the pass or fail results of the inspection.

In the first embodiment of the present invention, the inspection system is used to inspect transparent disks. In this configuration the light beam in the Surface Inspection Assembly originates in the laser, is transmitted through a filter, and is transmitted to the aperture of the Optical Scanner, which reflects the light beam off the moving polygonal scanner head, causing the light beam to sweep across the Scanning Optics. The Scanning Optics make the light beam normal to the surface of the disk and focused at the center of the disk media. On the opposite side of the disk, Detection Optics collimate the light beam and project it onto the Parallel Detector Array, which detects defects in the disk above a programmable threshold. Once the Optical Scanner beam completes one complete scan, the disk is then rotated to the next position, and the scanning continues in like manner until the entire surface of the disk has been inspected. The computer controls the rotation of the disk to assure the entire surface is scanned. At the same time the disk is rotating, the Edge Inspection Assembly simultaneously inspects both the inner and outer edges of the disk for defects above a programmable threshold. If either the Surface Inspection Assembly or the Edge Inspection Assembly detects a defect greater than their programmed thresholds, a fault signal is sent to the computer to indicate the disk failed the inspection.

In the second embodiment of the present invention, the inspection apparatus is used to inspect reflective disks. Reflective disks can be scanned using two different configurations of the inspection apparatus of the present invention. In the first configuration the apparatus is used to scan both sides of the reflective disk within the same scan. This is accomplished by placing the disk under test near the center of the scanning beam sweep, with its face normal to the direction of the sweep. Two mirrors are placed at 45 degree angles with respect to the two faces of the disk such that the Optical Scanner beam is reflected onto the two faces. The Scanning Optics and the mirrors focus the Optical Scanner beam on the two faces of the reflective disk. As the Optical Scanner beam begins its scan, the first mirror reflects the beam to the outer edge of the first face of the disk. The reflective face of the disk reflects the beam back to the mirror, which reflects the beam back to the Optical Scanner. This reflected beam is distinguished from the transmitted beam using a beam splitter between the laser and the Optical Scanner. The reflected beam is then projected on the Parallel Detector Array, which detects defects in the disk above a programmable threshold. As the Optical Scanner beam moves, the beam on the disk moves from outside to inside on this first side of the disk. The first side of the disk is completely scanned when the Optical Scanner beam has traveled about half of its scan distance. Near the center of the scan the Optical Scanner beam contacts the outside edge of the disk. As the Optical Scanner beam continues its scan, the second mirror reflects the Optical Scanner beam, beginning at the inside of the disk on the second face of the disk, and moves from inside to outside. By the time the Optical Scanner beam has completed one linear scan, both sides of the disk have been inspected along the scan line. The disk is then rotated to the next position, and the scanning continues in like manner until the entire surface of both sides of the disk have been simultaneously inspected. At the same time the disk is rotating, the Edge Inspection Assembly simultaneously inspects the outer edges of the disk for defects above a programmable threshold. If either the Surface Inspection Assembly or the Edge Inspection Assembly detects a defect greater than their programmed thresholds, a fault signal is sent to the computer to indicate that the disk failed the inspection.

In the second configuration of the second embodiment of the present invention, the disk is placed normal to the Optical Scanner beam, in the same position as the transparent disk of the first embodiment of the present invention. The disk reflects the beam, which is distinguished from the transmitted beam using a beam splitter between the laser and the Optical Scanner. The reflected beam is then projected on the Parallel Detector Array, which detects defects in the disk above a programmable threshold. With this configuration, only one side of the disk is inspected at a time, requiring the automatic media handler to turn the disk over after the first side is inspected for inspection of the second side, or requiring two separate scanning systems to inspect both sides simultaneously.

In the third embodiment of the present invention, the inspection system is used to inspect transparent flat panels, such as those commonly used in LCD panels. The size of a flat panel can be much greater than the size of disks commonly used in hard disk drives. An inspection system similar to that of the first embodiment could be used for small transparent flat panels where the size of the flat panel is smaller than the size of the Optical Scanner lens. However, many flat panels are larger than a practical lens, making a different method desirable to accommodate larger flat panels.

Placing the Optical Scanner at a distance from the Scanning Optics less than the focal length of the Scanning Optics causes the light beam to diverge at the Scanning Optics, making the beam sweep a distance larger than the diameter of the lens. The beam is focused at the center of the transparent flat panel media by the Scanning Optics. On the opposite side of the flat panel is a strip of a spherical mirror which reflects the divergent beam back through the Scanning Optics to the Optical Scanner. This reflected beam is distinguished from the transmitted beam using a beam splitter between the laser and the Optical Scanner. The reflected beam is then projected on the Parallel Detector Array, which detects defects in the disk above a programmable threshold. In this particular application, the flat panel is placed on an actuator that positions the flat panel such that the scanning begins at the top of the flat panel and moves down. Once the Optical Scanner beam completes one scan, the panel is raised to the next position, and the scanning continues in like manner until the entire surface of the flat panel has been inspected. The computer controls the movement of the flat panel to assure the entire surface is scanned. If the Surface Inspection Assembly detects a defect greater than its programmed threshold, a fault signal is sent to the computer to indicate the flat panel failed the inspection.

The foregoing and other objects, features and advantages will be apparent from the following description of the preferred embodiments of the invention as illustrated in the accompanying drawings.

BRIEF DESCRIPTION OF THE DRAWINGS

FIG. 8 is a block diagram of the Edge Inspection Assembly used in the first embodiment of the present invention shown in FIG. 3.

FIG. 8a is a cross-sectional view of the transparent disk shown in FIG. 8 showing how the waveguide properties of the transparent disk cause illumination of the inner edges with a light source shining on the outer edge.

FIG. 12 is a block diagram of the Surface Inspection Assembly used in the second embodiment of the present invention shown in FIG. 4.

FIG. 13a is a top view of the Optical Scanner and optics function in the Surface Inspection Assembly shown in FIG. 11 for reflective disks.

FIG. 13b is enlarged view of the circle in FIG. 13a showing how the beam is focused on the surface of the disk and reflected back.

FIG. 16b is a top view of the optics function of an alternative parallel detection configuration which detects changes in the amplitude and/or phase of the Optical Scanner beam.

FIG. 16c is a front view of another specific configuration of the Parallel Detector Array which detects changes in the amplitude and/or phase of the Optical Scanner beam.

FIG. 17 is a block diagram of the Surface Inspection Assembly used in third embodiment of the present invention shown in FIG. 14.

DESCRIPTION OF THE PREFERRED EMBODIMENTS

Figure 1:
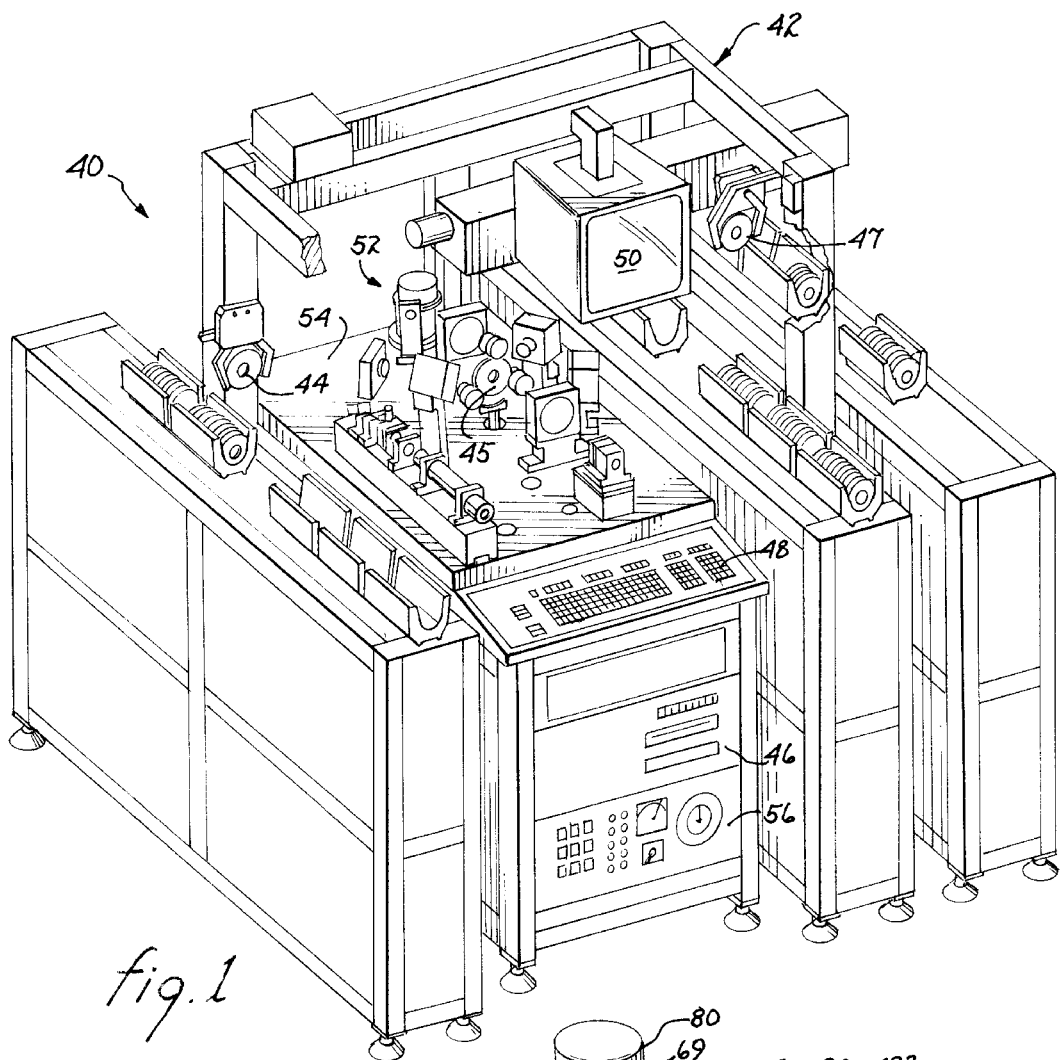
FIG. 1 is a perspective view of the optical inspection apparatus of the present invention.
Figure 1A:
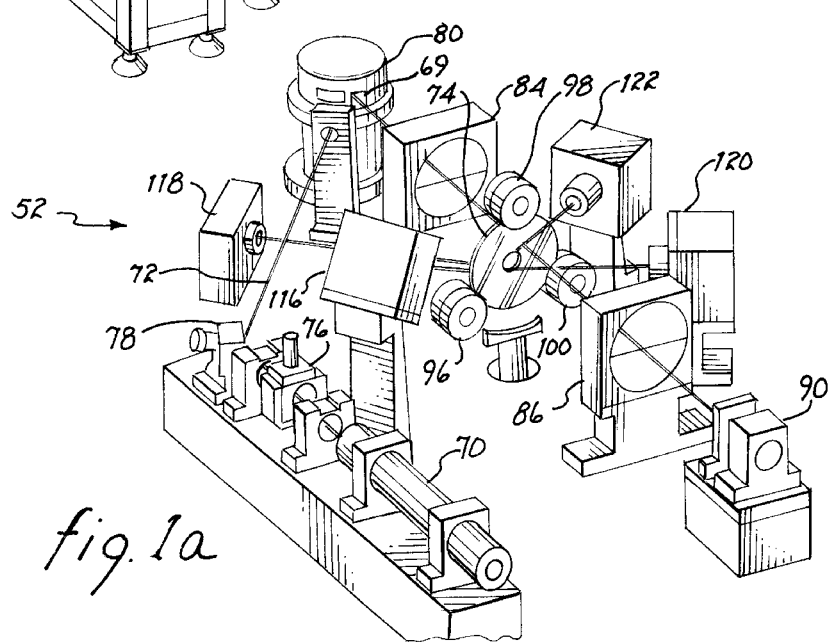
FIG. 1a is an enlarged view of the Optical Inspection Assembly shown in FIG. 1.
Figure 2:
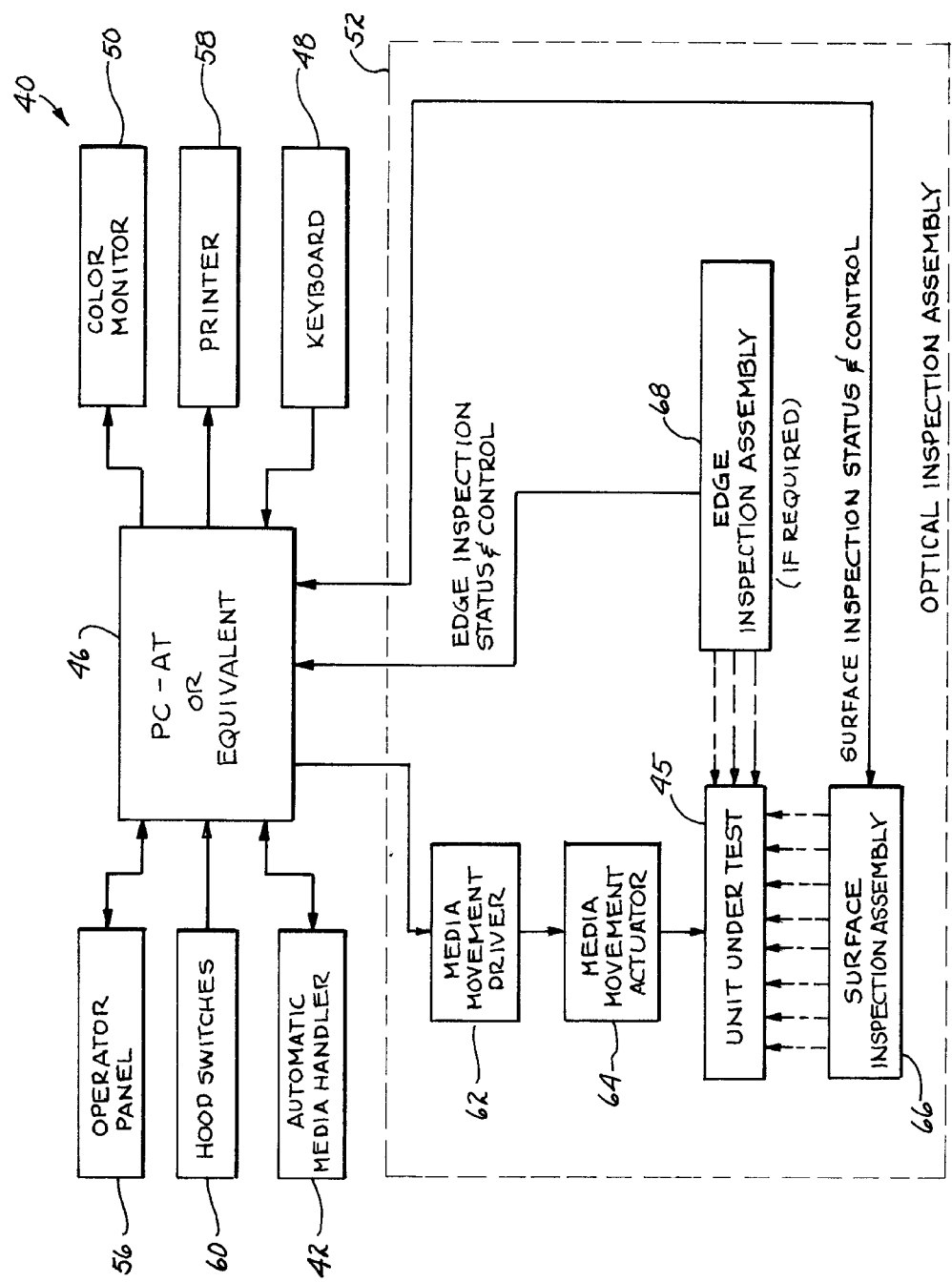
FIG. 2 is a block diagram of the optical inspection apparatus of FIG. 1.

FIG. 1 shows the optical inspection apparatus 40 of the present invention, comprising an IBM compatible PC-AT computer 46 or equivalent, a keyboard 48, a color monitor 50, an operator panel 56, an Optical Inspection Assembly 52 located on table 54, and an Automatic Media Handler 42 (typically a robot) to automatically load and unload the media to be inspected (44, 45, and 47) into the Optical Inspection Assembly 52. FIG. 1a is an enlarged view of the Optical Inspection Assembly 52 of FIG. 1, showing the specific configuration used in the first embodiment of the present invention for inspecting transparent disks. FIG. 2 is the block diagram of the apparatus 40 of the present invention, with numbers that correspond to numbers in FIG. 1 representing the same components. The apparatus shown in FIG. 2 includes a printer 58, and hood switches 60 for detecting when the apparatus 40 is ready for operation. These hood switches 60 act as safety devices, inhibiting operation of the apparatus 40 until the apparatus 40 is in the correct configuration with all hoods secured properly. The Optical Inspection Assembly 52 comprises a Media Movement Driver 62, a Media Movement Actuator 64, a Surface Inspection Assembly 66, an optional Edge Inspection Assembly 68, and the Unit Under Test 45.

The Automatic Media Handler 42 first loads the Unit Under Test 45 into the Optical Inspection Assembly 52. The Surface Inspection Assembly 66 then begins its scan of the surface of the Unit Under Test 45. At the same time the Edge Inspection Assembly 68, if present, begins inspection of the edges of the Unit Under Test 45. Both the Surface Inspection Assembly 66 and the Edge Inspection Assembly 68 perform only a linear inspection, and thus depend on the Media Movement Actuator 64 to move the Unit Under Test 45 such that the entire surface is inspected by the Surface Inspection Assembly 66, and such that the entire edge is inspected by the Edge Inspection Assembly 68 (if present).

The Surface Inspection Assembly 66 and the Edge Inspection Assembly 68 both have programmable thresholds that determine the characteristics of allowable defects. If either of these assemblies detects a defect greater than the programmed threshold, a fault signal is sent to the computer 46 to indicate that the inspection failed. The computer 46 causes the Automatic Media Handler 42 to place good units (those that pass inspection) in one place, and to place bad units (those that fail inspection) in a different place. In a fully automated system, an automated cart or conveyer would deliver uninspected units and take away both good and bad inspected units as the apparatus 40 requires.

The foregoing discussion applies to all configurations of the apparatus 40 of the present invention. The three distinct embodiments of the present invention relate to the different configurations and combinations of the Surface Inspection Assembly 66 and the Edge Inspection Assembly 68, which vary according to the physical configuration of the Unit Under Test 45. Note that the particular configuration shown in FIG. 1 and FIG. 1a for illustrative purposes is the first preferred embodiment of the present invention.

Figure 3:
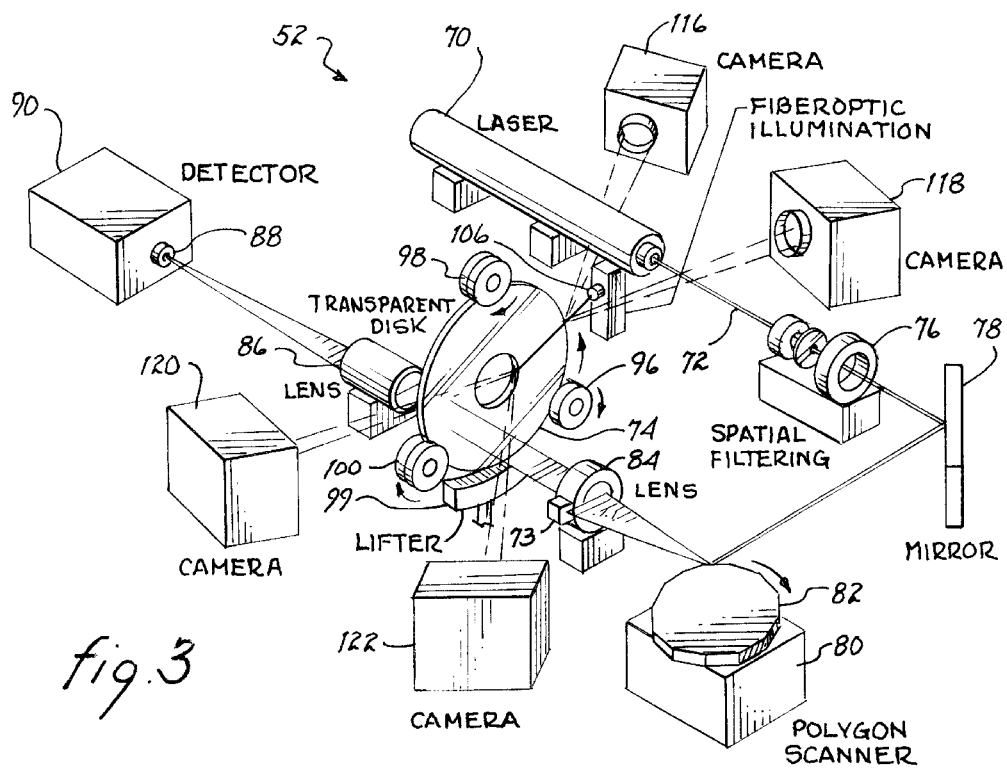
FIG. 3 is a perspective view of the first embodiment of the present invention for inspecting transparent disks.

In the first embodiment of the present invention, the apparatus 40 is used to inspect transparent disks. In this configuration, the Edge Inspection Assembly 68 of FIG. 2 is present, and includes simultaneous detection of defects on both the outer edges and the inner edges of the disk. The Optical Inspection Assembly 52 for this embodiment is shown in FIG. 3. A laser 70 provides the light beam 72 used to inspect the Transparent Disk 74. The laser 70 must have a minimum spatial and temporal coherence greater than the defects to be measured. The coherence of the laser 70 is related to its optical Signal to Noise (S/N) ratio, while the power of the laser 70 is related to its electrical S/N ratio. The light beam 72 passes through Filter Optics 76, which increases the spatial coherence of the beam 72 and shapes and directs the beam 72 to the mirror 78, which directs the beam 72 to an aperture 69 on Optical Scanner 80. The aperture 69 on Optical Scanner 80 is shown in FIG. 1 a. Referring again to FIG. 3, Optical Scanner 80 has a rotating polygonal head 82 with reflective faces. The beam passes through the aperture (not shown in FIG. 3) onto the rotating polygonal head 82, which causes the beam 72 to sweep across the Scanning Optics 84. If the polygonal head 82 rotates clockwise as shown, the sweep of the beam 72 will be from left to right on the Transparent Disk 74.

The Scanning Optics 84 are placed at the precise distance from the polygonal head 82 of Optical Scanner 80 defined by the focal length of the Scanning Optics 84. The Transparent Disk 74 is placed at this same distance from the Scanning Optics 84, such that the focal point of the beam is at the exact center of Transparent Disk 74. After passing through the focal point in the center of Transparent Disk 74, the beam 72 diverges and contacts Detection Optics 86, which is placed at a distance from the Transparent Disk 74 that corresponds to its focal length. The Detection Optics 86 cause each point along the beam scan to project on the Parallel Detector Array 88 within Detector 90, which is also placed at a distance from the Detection Optics 86 that corresponds to the focal length of Detection Optics 86.

Figure 11A:
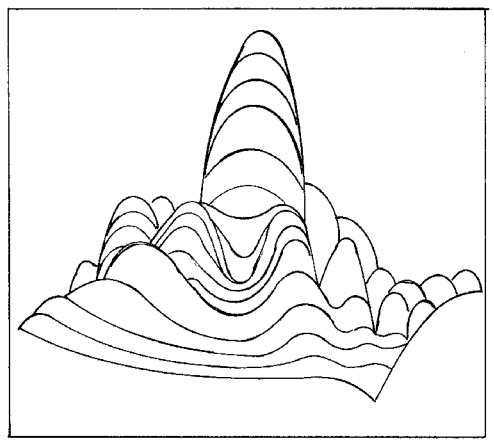
FIG. 11a is three dimensional representation of a typical Gaussian (distribution of light intensity (amplitude).
Figure 11B:
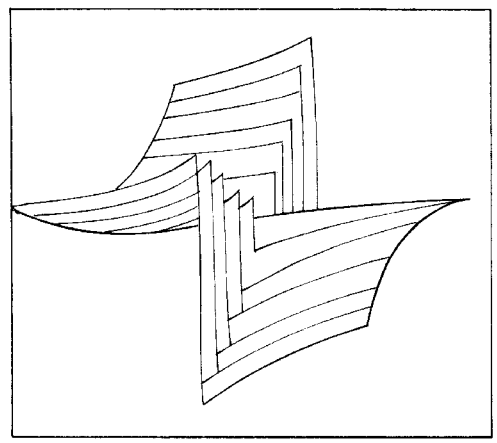
FIG. 11b is a three dimensional representation of a typical Gaussian distribution of light phase.
Figure 16:
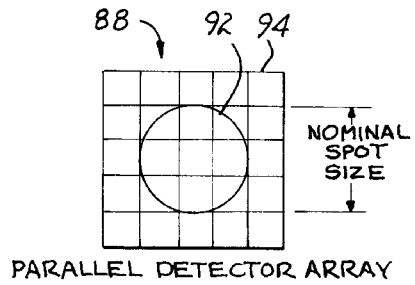
FIG. 16 is a front view of one specific configuration of the Parallel Detector Array which detects changes in the amplitude and/or phase of the Optical Scanner beam.

One specific implementation of Parallel Detector Array 88 is shown in more detail in FIG. 16. An array of light sensitive devices 94 is provided, typically a photodiode array. Each light sensitive device 94 provides an electrical signal proportional to the intensity of light it detects. A nominal beam spot 92 is shown, which is smaller than the matrix as shown. This type of a spot 92 of laser light on Parallel Detector Array 88 causes a two-dimensional response with respect to intensity or amplitude, which is represented in FIG. 11a. Likewise, this type of spot 92 causes a two-dimensional response with respect to changes of phase, which is represented in FIG. 11b. The changes of phase will create an interference pattern between the center and outer rim of the beam 72, causing a change in the ideal Gaussian distribution.

Figure 16A:
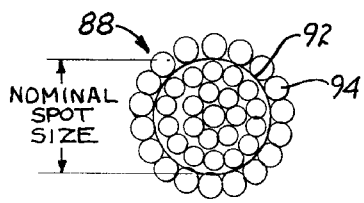
FIG. 16a is a front view of another specific configuration of the Parallel Detector Array which detects changes in the amplitude and/or phase of the Optical Scanner beam.

Note that the light sensitive devices 94 of Parallel Detector Array 88 could also be an array of CCDs, and could be arranged in any physical configuration, such as circular or concentric rings of individual detectors, as shown in FIG. 16a. In addition, two concentric ring detectors in the configuration shown in FIG. 16c could be used to form Parallel Detector Array 88. Detector 94a detects the center portion of the beam, while detector 94b detects the outer portion of the beam, which has nominal spot size 92 as shown.

FIG. 16b shows an alternative arrangement which uses two Parallel Detector Arrays 88. Beam 72 has a nominal spot size 92 as shown. Beam 72 is projected onto a transparent substrate 87 which has a small reflective portion 89, and is positioned at a 45 degree angle with respect to the beam 72 as shown. In this manner the center portion 85 of beam 72 is reflected off the reflective portion 89 of transparent substrate 87 to a Parallel Detector Array 88a as shown in the figure. The outer portion 83 of the beam 72 passes through the transparent substrate 87 onto a second Parallel Detector Array 88b. In this manner the two Parallel Detector Arrays 88a and 88b act in parallel to detect any change in the nominal Gaussian distribution of light within beam 72.

Note that the Parallel Detector Arrays 88a and 88b shown in FIG. 16b could be replaced with a single detector, since the two detectors 88a and 88b act in parallel, and can therefore detect with only two sensors changes in the nominal Gaussian distribution of the beam 72. Neither the number, type of device used nor the physical arrangement of these devices is critical to this invention. The primary inventive feature regarding the Parallel Detector Array 88 is the use of more than one optical detector in parallel to detect changes in a nominally Gaussian distribution of light within the spot of the optical beam 72.

By measuring changes in the Gaussian distribution of light, the apparatus 40 of the present invention has a much higher resolution than prior art optical inspection systems, which are limited by the diffraction limits of the optics and specific configuration of the system. By measuring changes in the Gaussian distribution of the beam 72, the apparatus 40 measures changes in the electromagnetic fields in a general point in space, which therefore removes the classical diffraction limit experienced by prior art systems. Since the Parallel Detector Array 88 can detect changes in both phase and amplitude of the nominal Gaussian distribution of light (phase changes are detected by interference between the center and rim of the beam), a change in the surface characteristics caused by even a very narrow or shallow defect will interfere with the rest of the field, and will be detected. This allows the lateral resolution of the apparatus 40 to be from 100 to 1000 times greater than the diffraction limit, since phase changes are detected as well as amplitude changes. In addition, the longitudinal sensitivity within the diffraction limit is interferometric, while the adjustment sensitivity is only dependent on the depth of field. These features provide for a highly sensitive inspection apparatus 40, which can detect any changes of the optical characteristics of the inspected surface on the order of 1/100 to 1/1000 of the diffraction limit in all three axes.

Figure 15C:
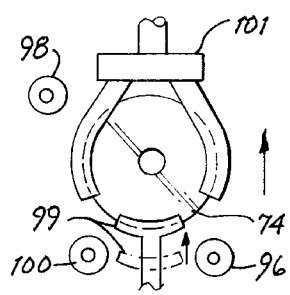
FIG. 15c is an elevational view of the disk and rollers of FIG. 15b showing how the movement of the roller shown in FIG. 15b and the operation of the lifter allow the automatic media handler to load and unload the disk into the apparatus of FIGS. 3 and 4.
Figure 15B:
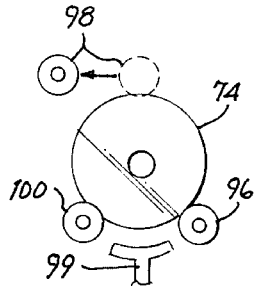
FIG. 15b is an elevational view of the disk and rollers of FIG. 15a showing how the top roller moves to facilitate loading and unloading of the disk by the Automatic Media Handler.
Figure 15D:
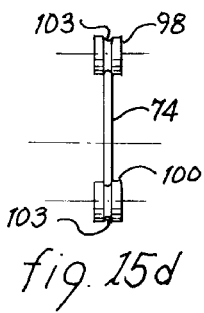
FIG. 15d is a side view of two of the rollers and the disk shown in FIG. 15a taken along the line 15d—15d showing the slot in the rollers for holding the disk in place during rotation.
Figure 15A:
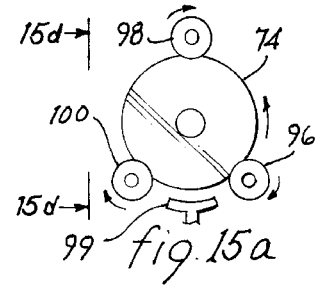
FIG. 15a is an elevational view of the disk of FIG. 3 and FIG. 4 showing the roller configuration which rotates the disk during inspection.

Referring again to FIG. 3, rollers 96, 98 and 100 comprise the Media Movement Actuator 64 shown in FIG. 2 for this particular embodiment of the present invention. Only one of these three rollers 96, 98 and 100 are motor-driven, with the computer 46 controlling the motor drive through communicating with the Media Movement Driver 62 as shown in FIG. 2. For illustration purposes, it will be assumed that roller 96 is the one roller that is driven by a motor, and that it rotates in a clockwise direction as shown. As the Optical Scanner 80 sweeps the beam 72 repeatedly from left to right on Transparent Disk 74, the computer 46 causes roller 96 to rotate clockwise, which causes Transparent Disk 74 to rotate counter-clockwise. In this manner the entire surface of Transparent Disk 74 is scanned when it has rotated one revolution. FIG. 3 shows a lifter 99, which acts in conjunction with the Automatic Media Handler 42 (not shown) to load untested disks into the Optical Inspection Assembly 52 and to unload tested disks from the Optical Inspection Assembly 52. The detailed operation of the loading and unloading function can be best understood in reference to FIGS. 15a–c. These three figures illustrate how the Transparent Disk 74 is unloaded from the Optical Inspection Assembly 52 by the Gripping Arm 101 of the Automatic Media Handler 42. FIG. 15a shows a Transparent Disk 74 while it is being rotated under test by rollers 96, 98 and 100. Lifter 99 is positioned away from the Transparent Disk 74 during testing. When testing is complete, the computer 46 stops driving roller 96, causing the rotation of the rollers 96, 98 and 100 to stop. The computer 46 then moves the roller 98 out of the way as shown in FIG. 15b. Once roller 98 is out of the way, the Gripping Arm 101 of Automatic Media Handler 42 is placed into the proper position, and lifter 99 then lifts the Transparent Disk 74 away from rollers 96 and 98, to a position where Gripping Arm 101 can close and thereby grip the Transparent Disk 74, as shown in FIG. 15c. This process is reversed for loading disks into the Optical Inspection Assembly 52. FIG. 15d shows a side view of the rollers 98 and 100 and the Transparent Disk 74 shown in FIG. 15a, illustrating the narrow slots or "V" grooves 103 used to hold the disk 74 in the proper position on the rollers 96, 98 and 100.

Figure 5:
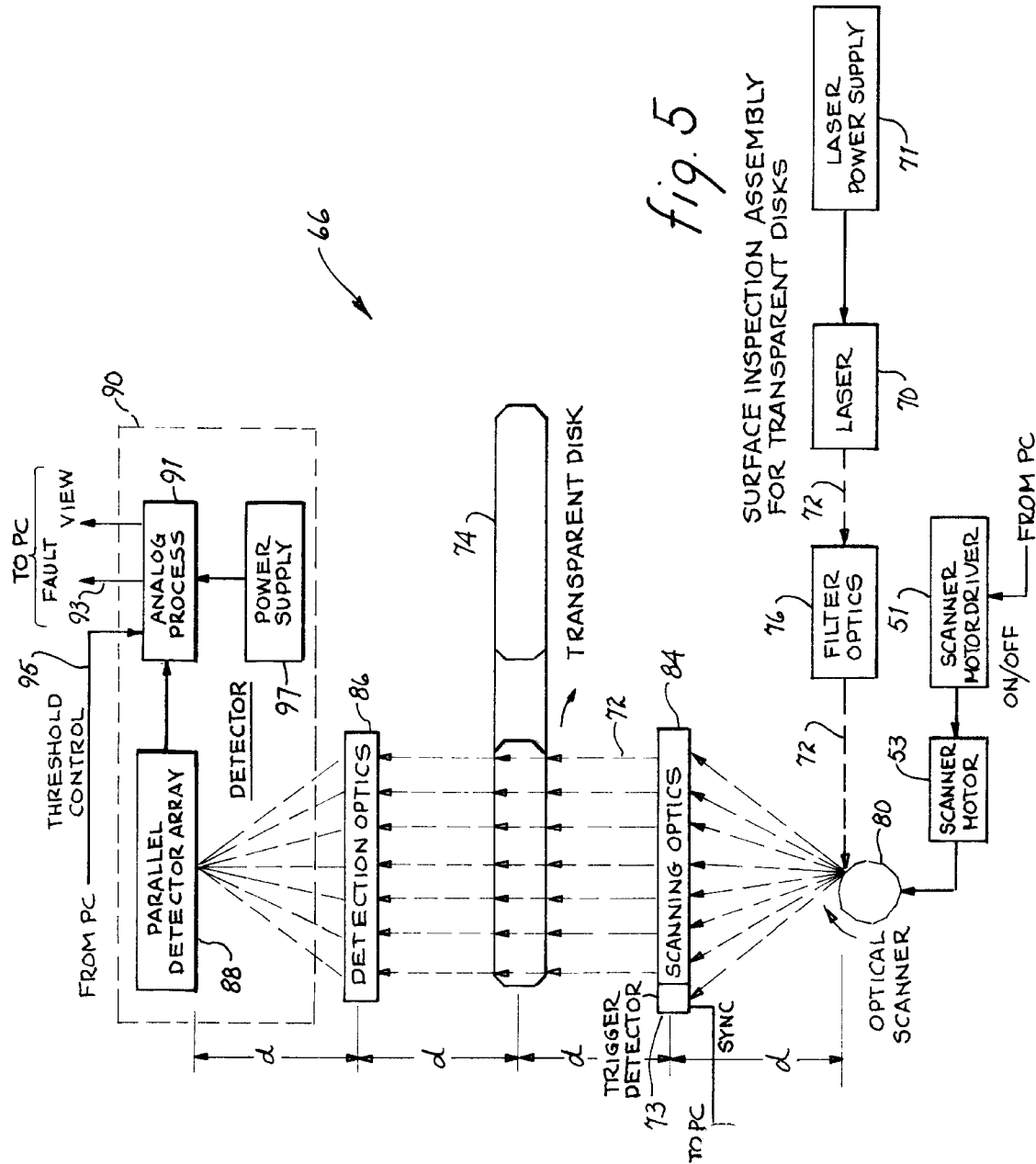
FIG. 5 is a block diagram of the Surface Inspection Assembly used in the first embodiment of the present invention shown in FIG. 3.

FIG. 5 shows the configuration of the Surface Inspection Assembly 66 shown in FIG. 2 used in the Optical Inspection Assembly 52 for the first embodiment of the present invention, which is used to inspect transparent disks. Note that many of the numbers in FIG. 5 correspond to components shown in FIG. 3. The laser 70 is powered by a Laser Power Supply 71, and provides beam 72, which passes through Filter Optics 76. The mirror 78 of FIG. 3 is not shown in FIG. 5. The light beam 72 contacts the Optical Scanner 80, which provides a linear scanning action of the beam 72 across Trigger Detector 73 and Scanning Optics 84. Trigger Detector 73 is placed at the beginning position of the scan path of beam 72, and provides an electrical SYNC signal to the computer 46 when the beam 72 contacts it to synchronize the sweep of beam 72 with the rotation of the Transparent Disk 74 and the output of Detector 90. Note that the Optical Scanner 80 can be switched on or off by the computer 46 giving the appropriate command to the Scanner Motor Driver 51, which controls the Scanner Motor 53. Also note that the Trigger Detector 73 can be mounted anywhere within the scan path of beam 72. In the configuration illustrated in the figures, Trigger Detector 73 is mounted on the side of the Scanning optics 84. The Trigger Detector 73 could, in the alternative, be placed in the scan path of beam 72 next to the Transparent Disk 74. By placing the Trigger Detector 73 next to the Scanning Optics 84, no optic field of Scanning Optics 84 is taken by Trigger Detector 73.

As shown in FIG. 5, the angle sweep of Optical Scanner 80 is converted by the Scanning Optics 84 to a sweep of parallel beams, each contacting the Transparent Disk 74 normal to its surface. The beam 72 continues through the Transparent Disk 74 to Detection Optics 86, which directs each beam to the Parallel Detector Array 88 of Detector 90. The nominal Gaussian output of Parallel Detector Array 88 is processed by analog circuitry in the Analog Process block 91, which is powered by Power Supply 97. Analog Process 91 receives a threshold control signal 95 from the computer 46 and detects any change in the Gaussian distribution of beam 72 which corresponds to a defect greater than the programmed threshold. When such a defect occurs, the Analog Process 91 signals the computer 46 that the inspection failed by asserting a Fault signal 93. The computer 46 will then nominally abort the inspection of the Transparent Disk 74, and cause the failed disk to be placed in the area of bad disks by the Automatic Media Handler 42.

Figure 6:
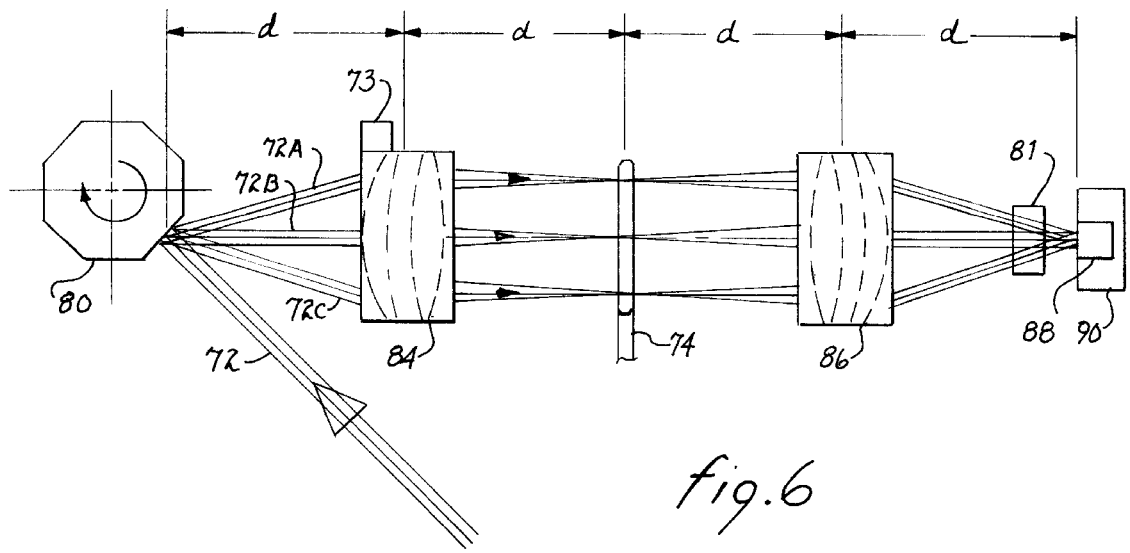
FIG. 6 is a top view of the Optical Scanner and optics function in the Surface Inspection Assembly shown in FIG. 5 for transparent disks.

FIG. 6 clearly represents the operation of the Scanning Optics 84 and the Detection Optics 86. With the configuration as previously described, the beam 72 is reflected off the Optical Scanner 80, and first contacts the Trigger Detector 73, then continues to scan across the Scanning Optics 84. Beam 72 first comes in contact with Scanning Optics 84 on the left side of the Scanning Optics 84, as represented by 72A in FIG. 6. Scanning Optics 84 focuses the beam to a small spot at the exact center of the Transparent Disk 74 as shown. After passing through the focal point at the center of the Transparent Disk 74, the beam 72A begins to diverge. The beam 72A then contacts Detection Optics 86, which directs the beam 72A to the Parallel Detector Array 88 within Detector 90. Note that Optional Detection Optics 81 may be used to magnify the beam 72, to correct for wandering of beam 72, or for other purposes as required.

As the Optical Scanner beam 72 continues its sweep, it will come to the position shown by 72B, and eventually to the position shown by 72C. Note that for each position of the beam 72, a different spot on the Transparent Disk 74 is in the path of the beam 72, and the resulting beam is projected onto the Parallel Detector Array 88 as shown. Note that this method can only be accomplished by placing the Optical Scanner 80 at a distance d from Scanning Optics 84 equal to the focal length of Scanning Optics 84. The center of the Transparent Disk 74 is located at this same distance from the Scanning Optics 84. In like manner, Detection Optics 86 is located this same distance from the center of the Transparent Disk 74, and the Parallel Detector Array 88 is located this same distance from the Detection Optics 86. In this configuration the size of the beam 72 at the Optical Scanner 80 is nominally the same size as the beam 72 at the Parallel Detector Array 88.

As the scanning of beam 72 takes place along a linear radius of the Transparent Disk 74, the Transparent Disk 74 is rotated one complete revolution to assure the entire disk surface is inspected. While this rotation of the disk takes place, both the inner and the outer edges of the disk are inspected for defects using the Edge Inspection Assembly 68, shown in detail in FIG. 8. The Edge Inspection Assembly 68 is comprised of an Outer Radius Inspection Assembly 128 and an Inner Radius Inspection Assembly 130. Within Outer Radius Inspection Assembly 128, a Power Supply 102 powers a light source 104, which passes through Projection Optics 106 to the outer edge of the Transparent Disk 74 as shown. Each disk nominally has two beveled edges 108 and 110 and a flat edge 109 on its outer edge as shown, and two beveled edges 112 and 114 and a flat edge 113 on its inner edge as shown. As shown in the figure, beveled edge 108 and half of flat edge 109 are inspected by Detector Optics #1 116, beveled edge 110 and the other half of flat edge 109 are inspected by Detector Optics #2 118, beveled edge 112 and half of flat edge 113 are inspected by Detector Optics #3 120, and beveled edge 114 and the other half of flat edge 113 are inspected by Detector optics #4 122. Detector Optics #1 116 and Detector Optics #2 118 project the image of the edge to be inspected onto detectors, the outputs of which are processed to determine if any defects occur greater than a programmable threshold. This detection and process step is represented by the Detectors and Process block 124. Likewise Detector Optics #3 120 and Detector Optics #4 122 go to a Detectors and Process block 126. Any defect in either the Outer Radius Inspection Assembly 128 or the Inner Radius Inspection Assembly 130 above their respective programmable thresholds is reported to the computer 46 as a fault, which causes the disk inspection to fail.

FIG. 8a illustrates how the single light source 104 within the Outer Radius Inspection Assembly 128 can be used to illuminate both the outer edges (108, 109 and 110) and the inner edges (112, 113 and 114) of the Transparent Disk 74 simultaneously. The light source shines through Projection Optics 106, which illuminates the outer edge of the Transparent Disk 74 as shown. Due to the transparency of Transparent Disk 74, the light that shines onto the outer edge of the Transparent Disk 74 is transmitted through the transparent disk medium to the inner edges 112, 113 and 114. FIG. 8a shows how the Transparent Disk 74 acts as a wave guide, directing the transmitted light to the inner edges of the disk. This feature allows for simultaneous illumination and inspection of both the inner edges (112, 113 and 114) and the outer edges (108, 109 and 110) with only one light source. This is significant since the addition of a second light source to inspect the inner edges would add to the expense and complexity of the apparatus 40, since this second light source would have to be positioned after the Transparent Disk 74 is loaded for testing, and removed prior to the Transparent Disk 74 being unloaded after testing.

Figure 9:
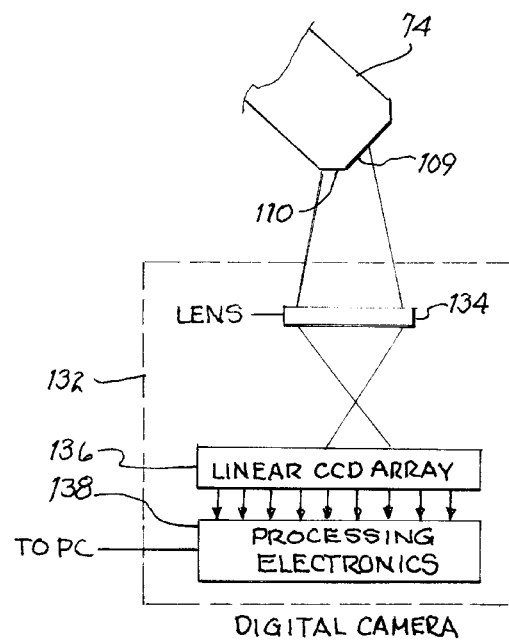
FIG. 9 is a partial perspective view of one particular implementation the outer radius inspection assembly shown in FIG. 8 using a camera having a linear CCD array.

Many of the components shown in FIG. 8 are also represented in FIG. 3 in their preferred configurations for the first embodiment of the present invention. Projection Optics 106 is a fiberoptic strand as represented in FIG. 3. Each of the Detector Optics 116, 118, 120 and 122 are digital CCD cameras in the first embodiment shown in FIG. 3. A detailed view of the operation of one of the digital CCD cameras is shown in FIG. 9. For illustrative purposes, inspection of edge 110 and half of edge 109 of the Transparent Disk 74 is shown. The digital CCD camera 132 has a single row of CCDs, known as a Linear CCD Array 136. The image of the edge 110 and the half of edge 109 of the Transparent Disk 74 to be inspected is focused by the lens 134 of the camera 132 onto the Linear CCD Array 136 as shown. The Processing Electronics 138 then processes the outputs from the Linear CCD Array 136 and asserts a fault signal to the computer 46 if a defect above a programmable threshold value exists. The Linear CCD Array 136 only detects a small portion of the edges as shown in FIG. 9, but the rotation of the disk for one revolution during inspection allows the camera 132 to inspect the entire edge during that one revolution. This occurs simultaneously for all edges 108, 109, 110, 112, 113 and 114 shown in FIG. 8, and occurs simultaneously with the inspection of the surface of the Transparent Disk 74 by the Surface Inspection Assembly 66.

Each inspection assembly in the apparatus 40 of the present invention has its own programmable threshold above which a fault will be signaled, causing the disk inspection to fail. In this manner the computer 46 only has to load the disk, rotate the disk, and monitor the outputs of each inspection assembly for faults. If a fault is signaled to the computer 46 prior to a full revolution being completed, the inspection fails and the disk is unloaded by the Automatic Media Handler 42 and placed in the place for "bad" disks. If the computer 46 completes a full rotation of the disk with no fault signal from any of the inspection assemblies, the disk passes the inspection and is unloaded by the Automatic Media Handler 42 and placed in the place for "good" disks.

Figure 10A:
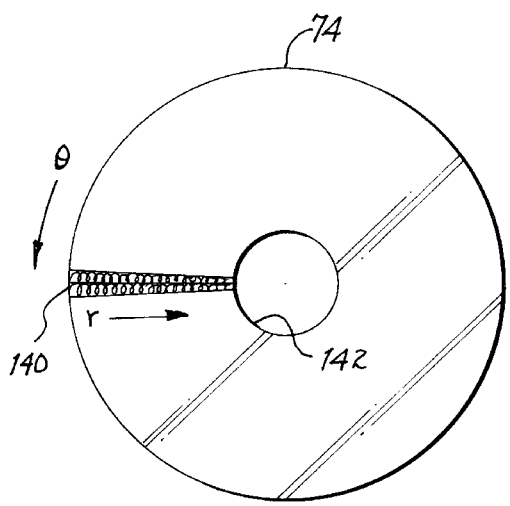
FIG. 10a is a front view of the transparent disk shown in FIG. 3 showing the scanning in the r direction, and rotation of the disk in the theta direction.
Figure 10B:
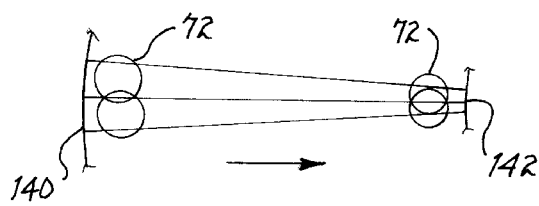
FIG. 10b is an enlarged view of the scanned portion of FIG. 10a showing how the combination of the linear travel of the beam and the rotation of the disk results in complete scanning of the entire surface of the disk.

FIGS. 10a and 10b illustrate how the combination of the scanning of the beam 72 and the rotation of the Transparent Disk 74 provide for a complete inspection of the entire surface of the Transparent Disk 74. As shown in FIG. 10a, the beam 72 scans in a line from left to right as shown by the r direction. At the same time the disk rotates in the theta direction shown in the figure. In this manner the disk is inspected in polar coordinates, with the r coordinate representing the position of the beam 72 in its scan path, and the theta coordinate representing the rotational position of the Transparent Disk 74.

The effect of this polar scanning technique is shown in FIG. 10b.

The beam is configured to scan along a radius of the Transparent Disk 74, from left to right as shown. The beam has a spot size which travels along this scan path. In order for the beam 72 to completely scan the entire surface of the Transparent Disk 74, the beam 72 must overlap somewhat with the previous scan path. Due to the circular configuration of the disk the outside circumference is significantly greater than the inside circumference, so a rotational change of position causes the outer edge to travel a farther distance than the inner edge. This means that the spot must overlap slightly on the outer edge 140 of the disk, which causes a much greater overlap on the inner edge 142 of the disk, as shown in FIG. 10b. This difference in overlap between the beam at the outer edge 140 and the inner edge 142 of the Transparent Disk 74 can be corrected using electronics or software to provide for accurate mapping of disk defects.

Figure 4:
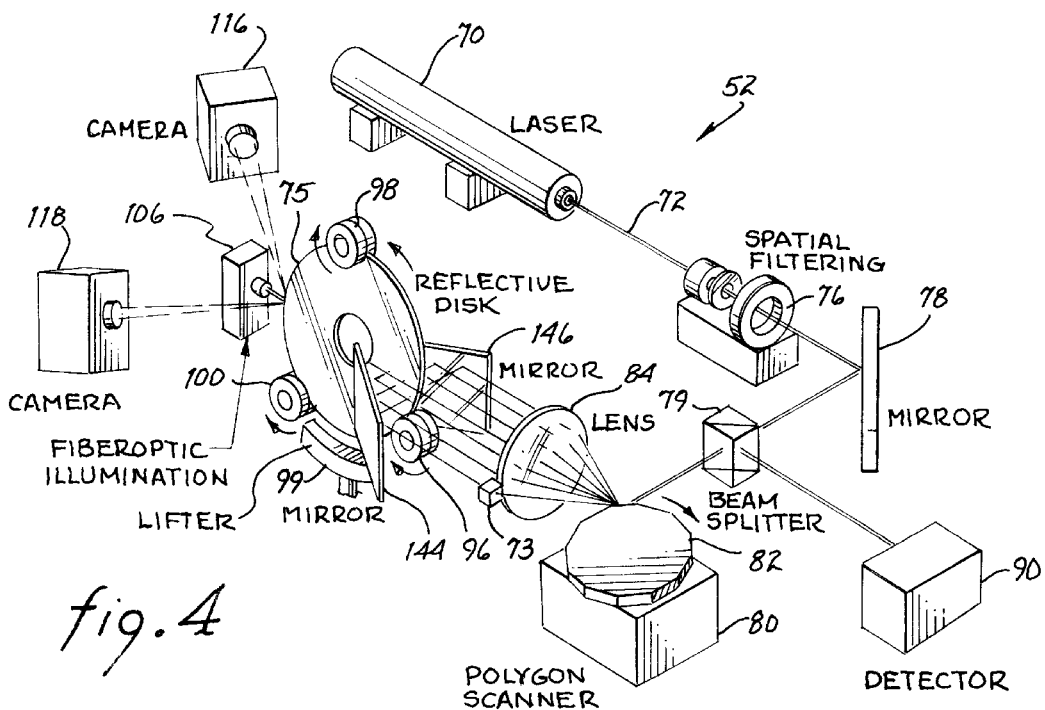
FIG. 4 is a perspective view of the second embodiment of the present invention for inspecting reflective disks.

The second embodiment of the apparatus of the present invention is used to inspect a reflective disk. In the system block diagram in FIG. 2, the only difference between this embodiment and the first embodiment is the change in the Optical Inspection Assembly 52. The Optical Inspection Assembly 52 for the preferred configuration of the second embodiment of the present invention is shown in FIG. 4, with components common to the first embodiment having the same numerical designators. Since the Reflective Disk 75 is reflective, the beam 72 will not pass through Reflective Disk 75, so the configuration of the first embodiment cannot be used to inspect a Reflective Disk 75. In this preferred configuration, both sides of the Reflective Disk 75 are inspected simultaneously by using two mirrors 144 and 146 to scan both sides of Reflective Disk 75 in one scan of beam 72. The mirrors 144 and 146 are placed at 45 degree angles with respect to the two faces of the Reflective Disk 75 so the reflected light beam 77 will be coincident with the transmitted light beam 72. In this configuration there is no separate Detection Optics, but the light beam 72 is reflected back to the Scanning Optics 84, which directs the reflected beam 77 (still coincident with the transmitted beam 72) to the Optical Scanner 80, then to a Beam Splitter 79. The Beam Splitter 79 directs the reflected beam 77 to the Parallel Detector Array 88 within Detector 90.

The Scanning Optics 84 are placed at the precise distance from the polygonal head 82 of the Optical Scanner 80 defined by the focal length of the Scanning Optics 84. The Reflective Disk 75 is placed at a position such that the path from the Scanning Optics 84 to the face of the Reflective Disk 75 along the entire scan of beam 72 is equal to the focal length of the Scanning Optics 84. In this manner beam 72 is focused precisely on both faces of the Reflective Disk 75.

FIG. 12 is a block diagram of the configuration of the Surface Inspection Assembly 66 shown in FIG. 2 used in the Optical Inspection Assembly 52 for this first configuration of the second embodiment as shown in FIG. 4. Note that all the numbers correspond to components shown in FIG. 4 or 5. The light beam generation, Optical Scanner 80, and Detector 90 have a configuration identical to that of the first embodiment shown in FIG. 5. The primary difference is the use of mirrors 144 and 146 to scan both sides of the Reflective Disk 75 in one scan, and the use of the Beam Splitter 79 to direct the reflected beam 77 to the Parallel Detection Array 88 within Detector 90.

FIG. 13a clearly represents the operation of the Scanning Optics 84 and the Beam Splitter 79 of the Surface Inspection Assembly 66 shown in FIG. 12. With this configuration, the beam 72 is reflected off the Optical Scanner 80, and first contacts the Trigger Detector 73, then continues to scan across the Scanning Optics 84. Beam 72 first comes in contact with Scanning Optics 84 on the left side of the Scanning Optics 84, as represented by A in FIG. 13a. The beam A contacts the mirror 144 as shown, which focuses beam A on the surface of Reflective Disk 75, which reflects the beam A back along a path coincident with the transmitted beam A. This is shown in more detail in FIG. 13b. This reflected beam 77 travels coincident with the transmitted beam 72 until it contacts the Beam Splitter 79, which directs the reflected beam 77 to the Parallel Detector Array 88 within the Detector 90.

As the Optical Scanner beam 72 continues its sweep, it will come to the position shown by beam B, then to the position shown by beam C, and eventually to the position shown by beam D. Note that for each position of the beam 72, a different spot on the Reflective Disk 75 is in the path of the beam 72, and the resulting reflected beam 77 is projected onto the Parallel Detector Array 88 by the Beam Splitter 79 as shown. Note that this method can only be accomplished by placing the Optical Scanner 80 at a distance d from Scanning Optics 84 equal to the focal length of Scanning Optics 84. The surface of the Reflective Disk 75 is located at this same distance from the Scanning Optics 84 after reflection in mirrors 144 and 146. In other words, the distance a+b as shown in FIG. 12 must equal the distance d.

Since the Scanning Optics 84 also plays the role of Detection Optics due to the reflected beam 77, the size of the beam 72 at the Optical Scanner 80 is the same as the size of the beam 72 at the Parallel Detector Array 88. Note that Optional Detection Optics 81 may be used for magnification, to correct beam wandering, or for other purposes as required.

FIG. 4 shows only two cameras for edge inspection rather than the four employed by the first embodiment and shown in FIGS. 3 and 8. The difference is that the second embodiment, which deals with a Reflective Disk 75, can only be inspected on the outer edge as shown in FIG. 4. Thus, in the Edge Inspection Assembly 68 shown in FIG. 8, only the Outer Radius Inspection Assembly 128 is present, since the Reflective Disk 75 cannot act as a waveguide to shine light on the inner edges 112 and 114 as shown in FIG. 8a. Inspection of the inner edges 112 and 114 would take a second light source in the Inner Radius Inspection Assembly 130, which would be positioned after the Reflective Disk 75 is in place. While this is an obvious modification to the apparatus 40 of the present invention, this feature is not shown in the figures.

Figure 7:
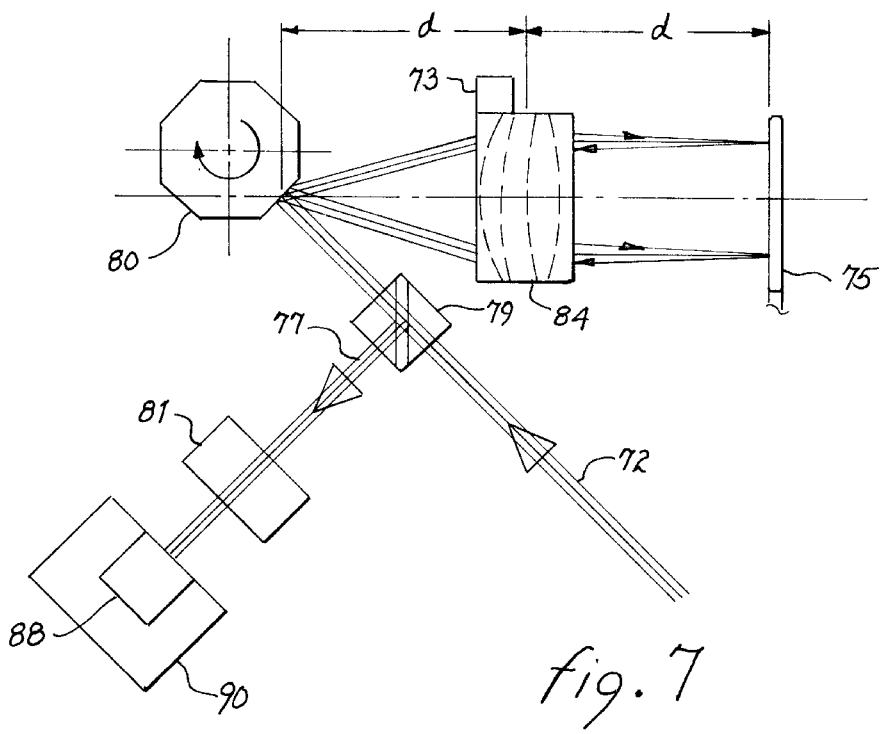
FIG. 7 is a top view of the Optical Scanner and optics function in an alternative configuration of the Surface Inspection Assembly used for inspecting reflective disks.

As FIGS. 12 and 13a clearly show, this first configuration of the second embodiment allows inspection of both sides of the reflective disk with one scan. In a second configuration of the second embodiment, as shown in FIG. 7, the Surface Inspection Assembly 66 does not have the mirrors that allow the scanning of both sides at once, but the Reflective Disk 75 is inspected one side at a time. When the apparatus 40 completes inspection of one side, it then turns the Reflective Disk 75 and inspects the second side. The operation of all the other features of this second configuration are identical to those explained in relation to FIGS. 12 and 13a. In addition, two separate scanning systems could be used in the configuration shown in FIG. 7 to accomplish scanning of both sides of the Reflective Disk 75 simultaneously.

The operation of rollers 96, 98 and 100, and lifter 99 is identical to that described for the first embodiment, with the difference being the orientation of the rollers to accommodate the Reflective Disk 75, which must be mounted substantially parallel to the beam 72 if simultaneous inspection of both sides of the disk is desired.

Figure 14:
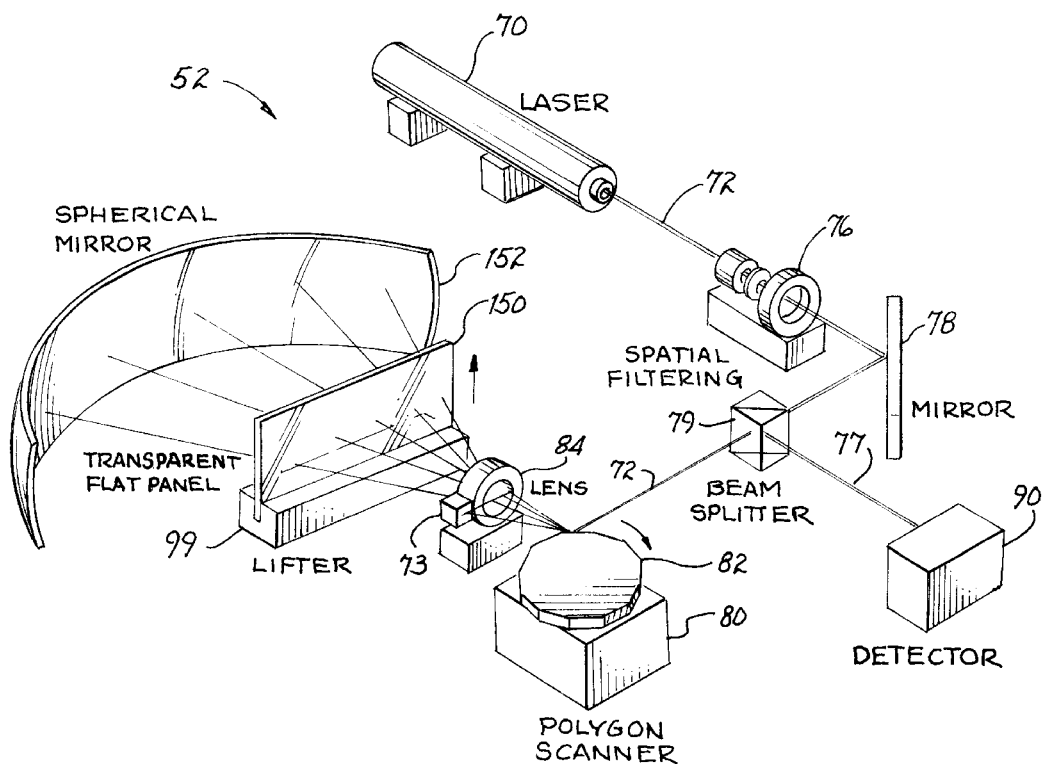
FIG. 14 is a perspective view of the third embodiment of the present invention for inspecting transparent flat panels.

In the third embodiment of the present invention, the apparatus 40 is used to inspect transparent flat panels. Referring to FIG. 2, the Edge Inspection Assembly 68 is not required for the inspection of a transparent flat panel. A perspective view of the Optical Inspection Assembly 52 for this third embodiment is shown in FIG. 14. Note that the Surface Inspection Assembly 66 is the only component of the Optical Inspection Assembly 52 since inspection of the edges of a Transparent Flat Panel 150 is not required.

Figures 18, 18A:
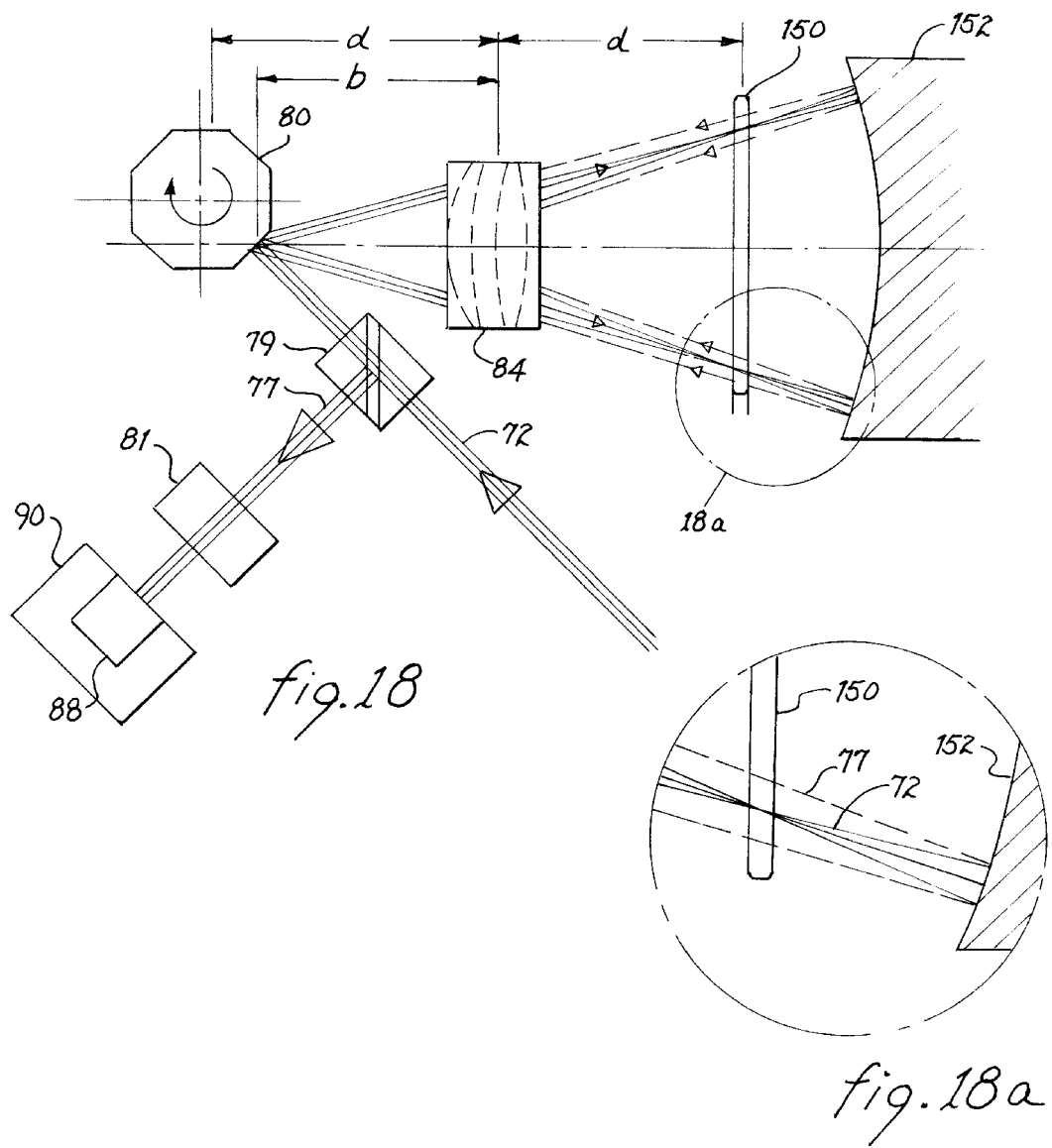
FIG. 18 is a t view of the Optical Scanner and optics function in the Surface Inspection Assembly shown in FIG. 17 for transparent flat panels.
FIG. 18a is an enlarged view of the circular area shown in FIG. 18.

The Surface Inspection Assembly 66 for this third embodiment is shown in FIG. 17. The operation of all the components in FIGS. 14 and 17 that are the same as those shown in FIGS. 4 and 12 are identical. The primary difference is that the Scanning Optics 84 in FIG. 12 is located at a distance d from the Optical Scanner 80 equal to the focal length of Scanning Optics 84. This configuration makes the beam exit the Scanning Optics 84 in a direction perpendicular to its face. This method works well for small items such as disks which are not larger than the size of a practical lens. However, a Transparent Flat Panel 150 may be considerably larger than the size of a practical lens. For this reason the Scanning Optics 84 are placed in a position relative to the Optical Scanner 80 which is less than the focal length of Scanning Optics 84. This relationship is shown in FIG. 18 by the distance b from the Optical Scanner 80 to the Scanning Optics 84 being less than the focal length d of Scanning Optics 84. This arrangement causes the beam 72 to diverge at the Scanning Optics 84 as shown in FIG. 17, rather than traveling in parallel paths which are perpendicular to the Scanning Optics 84. This feature allows the Scanning Optics 84 to scan a Flat Panel 150 that is larger than the Scanning Optics 84. The beam 72 is projected by Scanning Optics 84 at the exact center of Transparent Flat Panel 150. After the beam 72 passes through Transparent Flat Panel 150, it begins to diverge, and contacts Spherical Mirror 152. The Spherical Mirror 152 reflects beam 72, and this reflected beam 77 is directed back to the Scanning Optics 84. This is shown in more detail in FIG. 18a. Referring again to FIGS. 17 and 18, a Beam Splitter 79 is used to distinguish the reflected beam 77 from the transmitted beam 72, and to direct the reflected beam 77 to the Parallel Detector Array 88 within Detector 90. The Detector 90 functions the same as for the first and second embodiments.

Since the Transparent Flat Panel 150 is rectangular rather than circular, the Media Movement Actuator 64 shown in FIG. 2 for the third embodiment is different than the rollers used for inspecting disks in the first and second embodiments. The Media Movement Actuator 64 for the third embodiment is a lifter 99 as shown in FIG. 14. The lifter 99 in the first and second embodiment was used to facilitate loading and unloading of the disks into the rollers. The lifter 99 for the third embodiment differs from that used in the first and second embodiment in that it moves the Transparent Flat Panel 150 during the inspection rather than during loading and unloading of the Transparent Flat Panel 150. For example, during inspection, the lifter 99 positions the Transparent Flat Panel 150 such that the first scan of beam 72 scans the uppermost row of the Transparent Flat Panel 150. As the beam 72 scans the Transparent Flat Panel 150, the lifter 99 gradually raises the Transparent Flat Panel 150 such that all portions of the Transparent Flat Panel are scanned by the beam 72.

Figure 19:
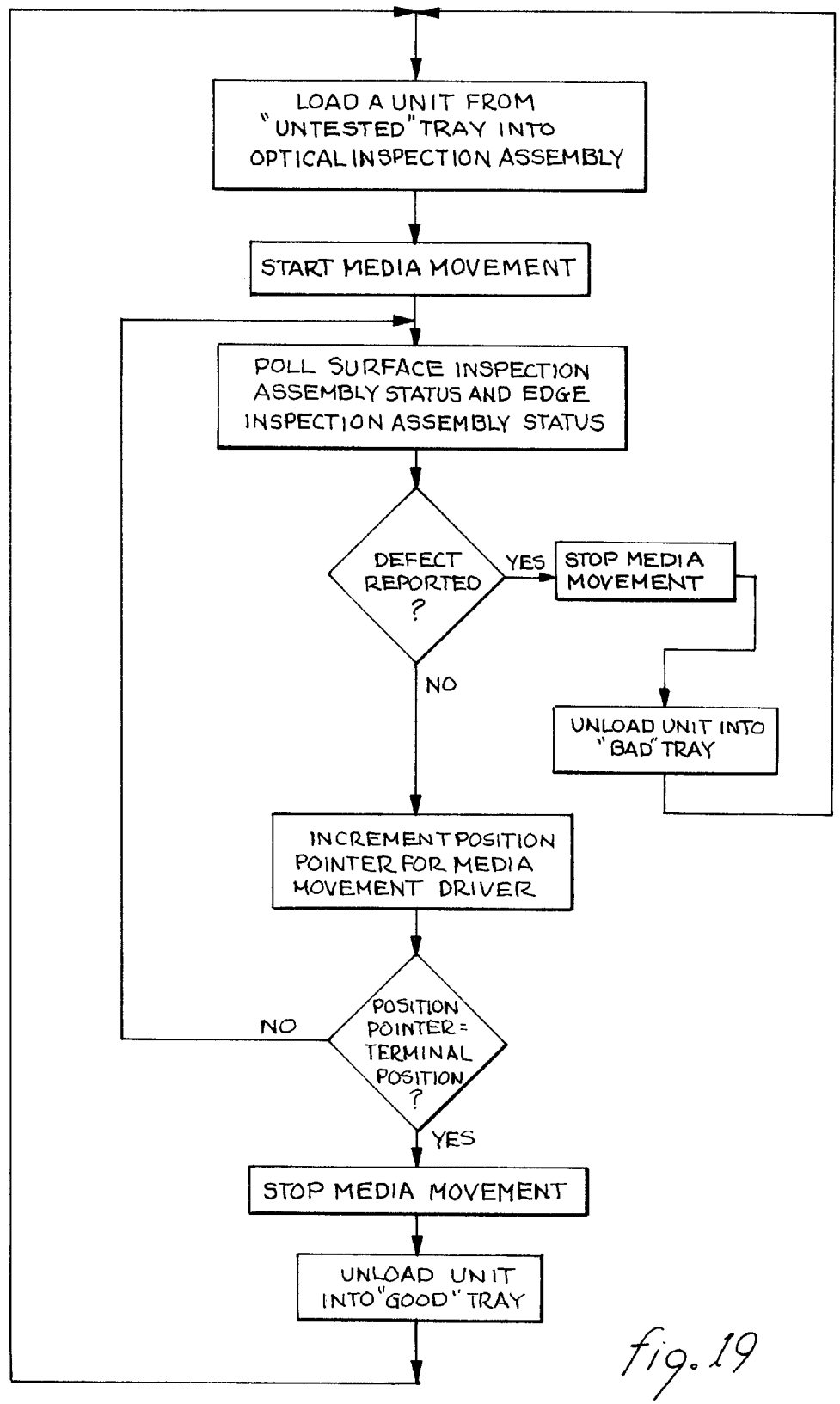
FIG. 19 is a flow chart of the control software operation for the apparatus of the present invention.

One advantage of the configuration of these three embodiments of the apparatus 40 of the present invention is that, regardless of the particular configuration of the Surface Inspection Assembly 66 and media, the main control software for computer 46 which controls the apparatus 40 can be identical for all three embodiments. As shown in FIG. 19, the function blocks of the control software are the same regardless of the specific embodiment implemented. The individual device driver software for directing the movement of the Automatic Media Handler 42, or the Media Movement Driver 62 will vary according to the embodiment implemented, but do not directly affect the operation of the main control software. The specific implementation shown in FIG. 19 assumes that the computer 46 will poll the Surface Inspection Assembly 66 and the Edge Inspection Assembly 68 to determine whether a defect is reported by either of these assemblies. In an alternative arrangement, the Fault output 93 of the Surface Inspection Assembly 66 and the Fault output 93 of the Edge Inspection Assembly 68 are interrupt-driven inputs to computer 46, which report a fault by interrupting program execution of the computer 46. In this configuration the computer 46 simply completes the movement of the media, then checks a software flag to determine whether a fault was detected during the scan.

The automation of apparatus 40 provided by computer 46 and Automatic Media Handler 42 provides for high-speed inspection of apparatus 40, which suits the apparatus 40 well to a speed-sensitive production environment.

While the invention has been described in its preferred embodiments, it is to be understood that the words which have been used are words of description rather than limitation, and that changes may be made within the purview of the appended claims without departing from the true scope and spirit of the invention in its broader aspects.

What is claimed is:

1. An optical inspection apparatus for inspecting flat, polished media comprising, in combination:

computer means for controlling said apparatus;

operator interface means coupled to said computer means for providing input data from an operator to said computer means and for providing output data from said computer means to said operator;

an optical inspection assembly, coupled to said computer means having output means for reporting to said computer means results of an inspection performed by said optical inspection assembly, comprising inspection means consisting of detector means for detecting changes of a nominal Gaussian distribution of a light beam; and a unit under test which is placed in said optical inspection assembly to inspect said unit under test for defects.

2. The apparatus of claim 1 further comprising automatic media handling means coupled to said computer means for loading under control of said computer means said unit under test into said optical inspection assembly and for unloading under control of said computer means said unit under test out of said optical inspection assembly.

3. The apparatus of claim 1 wherein said computer means comprising, in combination:

an IBM compatible personal computer; and control software means loaded into memory of said IBM compatible personal computer for determining function and sequence of operations of said apparatus.

4. The apparatus of claim 3 wherein said control software means comprising:

a main control program; and a plurality of device drivers which provide subroutines for said main control program and which control individual components of said apparatus.

5. The apparatus of claim 1 wherein said computer means periodically polls said output means of said optical inspection assembly to determine whether a defect has been detected by said optical inspection assembly.

6. The apparatus of claim 1 wherein said output means of said optical inspection means is coupled to said computer means such that said output means interrupts said computer means when a defect is detected by said optical inspection assembly.

7. The apparatus of claim 1 wherein said operator interface means comprising, in combination:

keyboard means coupled to said computer means for providing said input data from said operator to said computer means; and display means coupled to said computer means for displaying said output data from said computer means to said operator.

8. The apparatus of claim 7 wherein said operator interface means further comprising printer means for printing said output data from said computer means.

9. The apparatus of claim 7 wherein said operator interface means further comprising operator panel means having knobs and switches for selecting one of a plurality of detection thresholds for said optical inspection assembly.

10. The apparatus of claim 7 including means for permitting said operator to select one of a plurality of detection thresholds for said optical inspection assembly via said keyboard means.

11. The apparatus of claim 2 wherein said automatic media handling means comprising, in combination:
at least one input tray wherein said unit under test is placed prior to inspection by said apparatus;
at least one movable gripper hand located in proximity to said input tray for gripping and transporting said unit under test from said input tray to said optical inspection assembly;
a first output tray located in proximity to said movable gripper hand such that said unit under test is moved from said optical inspection assembly to said first output tray by said movable gripper hand if said output of said optical inspection assembly signals to said computer means that said unit under test has no defects; and
a second output tray located in proximity to said movable gripper hand such that said unit under test is moved from said optical inspection assembly to said second output tray by said movable gripper hand if said output of said optical inspection assembly signals to said computer means that said unit under test has defects.

12. The apparatus of claim 1 wherein said optical inspection assembly comprising, in combination:
media movement actuator means in physical proximity to said inspection means for moving said unit under test to allow said inspection means to fully inspect said unit under test for defects; and
media movement driver means electrically coupled to said media movement actuator means and to said computer means for allowing said computer means to control said media movement actuator means by providing appropriate commands to said media movement driver means.

13. The apparatus of claim 12 wherein said inspection means comprises surface inspection assembly means for inspecting at least one flat surface of said unit under test for defects while said media movement actuator means moves said unit under test.

14. The apparatus of claim 13 wherein said inspection means further comprises an edge inspection assembly means in physical proximity to said surface inspection assembly means for inspecting at least one edge of said unit under test for defects while said media movement actuator means moves said unit under test.

15. The apparatus of claim 12 wherein said unit under test comprising a round disk having an outer edge and a hole in a center portion and wherein said media movement actuator means comprising at least one actuated roller and motor means for driving said actuated roller for turning said round disk.

16. The apparatus of claim 15 wherein said media movement actuator means further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

17. The apparatus of claim 16 wherein said actuated roller and said idler roller both having notch means in their circumferential faces in which said outer edge of said round disk is placed for preventing said round disk from slipping off said actuated roller and said idler roller during rotation.

18. The apparatus of claim 12 wherein said unit under test comprising a rectangular flat panel and wherein said media movement actuator means comprising a lifter having a notch wherein an edge of said flat panel is placed and wherein said optical inspection assembly providing a linear sweep of a light beam on a flat surface of said flat panel, said lifter having a range of motion in a direction normal to a plane created by said linear sweep of said light beam, said lifter being coupled to and controlled by said computer means.

19. The apparatus of claim 13 wherein said surface inspection assembly means comprising, in combination:
a light source providing said light beam;
optical scanner means having an aperture in physical proximity to said light source for permitting said light beam to contact said aperture on said optical scanner and for reflecting said light beam thereby providing a linear sweep of said light beam;
scanning optics means having a front face portion and a rear face portion for permitting said linear sweep of said light beam to contact said front face portion of said scanning optics means for causing said light beam that contacts said front face portion to exit said rear face portion and to contact said flat surface of said unit under test;
trigger detector means coupled to said computer means and placed within said linear sweep of said light beam for providing a synchronizing electrical signal to said computer means for indicating a position of said light beam along said linear sweep;
detection optics means having a front face portion and a rear face for permitting said light beam after contacting said unit under test to contact said rear face portion and exit said front face portion; and
said detector means for permitting said light beam exiting said front face portion of said detection optics means to be received by said detector means for detecting changes of a nominal Gaussian distribution of said light beam, said changes corresponding to and identifying defects in said flat surface of said unit under test.

20. The apparatus of claim 19 wherein said light source comprising a laser diode and said light beam comprising a laser beam from said laser diode.

21. The apparatus of claim 19 wherein said light source comprising a helium-neon laser, and said light beam comprising a laser beam from said helium-neon laser.

22. The apparatus of claim 19 wherein said optical scanner means having a motor-driven polygonal head coupled to said computer means and having reflective faces such that said light beam contacts said reflective faces of said polygonal head through said aperture, and having means for rotating said polygonal head for causing said light beam reflected off said reflective faces to create said linear sweep of said light beam across said scanning optics means.

23. The apparatus of claim 22 wherein said motor-driven polygonal head is turned on and off by said computer means.

24. The apparatus of claim 19 wherein said aperture of said optical scanner means being located at a distance from said scanning optics means equal to the focal length of said scanning optics means.

25. The apparatus of claim 24 wherein said scanning optics means direct said light beam entering said front face portion such that said light beam exits said rear face portion in a direction normal to the focal plane of said scanning optics means.

26. The apparatus of claim 19 wherein said scanning optics means focus said light beam on said flat surface of said unit under test.

27. The apparatus of claim 19 wherein said trigger detector means comprising an optical sensor having an electrical output corresponding to the presence of said light beam on said optical sensor which is coupled to said computer means.

28. The apparatus of claim 27 wherein said optical sensor comprising a photodiode.

29. The apparatus of claim 27 wherein said optical sensor comprising a charge-coupled device (CCD).

30. The apparatus of claim 19 wherein said scanning optics means having a function as said detection optics means due to said light beam being projected by said scanning optics means to a reflective unit under test which reflects said light beam back to said scanning optics means.

31. The apparatus of claim 19 wherein said detector means comprising, in combination:
   at least two optical detectors having electrical outputs, said optical detectors functioning in parallel; and
   electronic circuitry means for processing said electrical outputs of said optical detectors and generating an electrical signal to said computer means comprising, in combination:
      first input means coupled to said electrical outputs of said optical detectors for monitoring said electrical outputs;
      second input means coupled to said computer means for receiving a threshold value from said computer means;
      processing means coupled to said first input means and to said second input means for measuring said electrical outputs of said optical detectors and for determining the existence of changes in said nominal Gaussian distribution of said light beam above said threshold value on said second input means; and
      output means coupled to said computer means for signaling an occurrence of a change above said threshold value to said computer means.

32. The apparatus of claim 31 wherein said optical detectors comprise photodiodes.

33. The apparatus of claim 31 wherein said optical detectors comprise charge-coupled devices (CCDs).

34. The apparatus of claim 31 wherein said optical detectors are arranged in rows and columns to form a substantially square matrix.

35. The apparatus of claim 31 wherein said optical detectors are arranged in a series of concentric circular rings.

36. An optical detection device for detecting changes in a nominal Gaussian distribution of a light beam comprising, in combination, means for detecting changes in said nominal Gaussian distribution of said light beam, said detecting means comprising at least two optical detectors coupled together to function in parallel to detect changes in said nominal Gaussian distribution of said light beam.

37. The device of claim 36 wherein said optical detectors comprise photodiodes.

38. The device of claim 36 wherein said optical detectors comprise charge-coupled devices (CCDs).

39. The device of claim 36 wherein said optical detectors are arranged in rows and columns to form a substantially square matrix.

40. The device of claim 36 wherein said optical detectors are arranged in a series of concentric circular rings.

41. The apparatus of claim 19 further comprising filter optics means for increasing spatial coherence of said light beam.

42. A method for inspecting flat, polished media using an optical inspection apparatus including the steps of:
   providing computer means for controlling said apparatus;
   providing operator interface means coupled to said computer means for providing input data from an operator to said computer means and for providing output data from said computer means to said operator;
   providing an optical inspection assembly, coupled to said computer means having output means for reporting to said computer means results of an inspection performed by said optical inspection assembly, comprising inspection means consisting of detector means for detecting changes of a normal Gaussian distribution of a light beam; and
   providing a unit under test which is placed in said optical inspection assembly to inspect said unit under test for defects.

43. The method of claim 42 further comprising the step of providing automatic media handling means coupled to said computer means for loading under control of said computer means said unit under test into said optical inspection assembly and for unloading under control of said computer means said unit under test out of said optical inspection assembly.

44. The method of claim 42 wherein said computer means comprising, in combination:
   an IBM compatible personal computer; and
   control software means loaded into memory of said IBM compatible personal computer for determining function and sequence of operations of said apparatus.

45. The method of claim 42 wherein said computer means periodically polls said output means of said optical inspection assembly to determine whether a defect has been detected by said optical inspection assembly.

46. The method of claim 42 wherein said output means of said optical inspection means is coupled to said computer means such that said output means interrupts said computer means when a defect is detected by said optical inspection assembly.

47. The method of claim 42 wherein said operator interface means comprising, in combination:
   keyboard means coupled to said computer means for providing said input data from said operator to said computer means; and
   display means coupled to said computer means for displaying said output data from said computer means to said operator.

48. The method of claim 47 wherein said operator interface means further comprising operator panel means having knobs and switches for selecting one of a plurality of detection thresholds for said optical inspection assembly.

49. The method of claim 47 including means for permitting said operator to select one of a plurality of detection thresholds for said optical inspection assembly via said keyboard means.

50. The method of claim 43 wherein said automatic media handling means comprising, in combination:
   at least one input tray wherein said unit under test is placed prior to inspection by said apparatus;
   at least one movable gripper hand located in proximity to said input tray for gripping and transporting said unit under test from said input tray to said optical inspection assembly;
   a first output tray located in proximity to said movable gripper hand such that said unit under test is moved from said optical inspection assembly to said first output tray by said movable gripper hand if said output of said optical inspection assembly signals to said computer means that said unit under test has no defects; and
   a second output tray located in proximity to said movable gripper hand such that said unit under test is moved from said optical inspection assembly to said second output tray by said movable gripper hand if said output of said optical inspection assembly signals to said computer means that said unit under test has defects.

51. The method of claim 42 wherein said optical inspection assembly comprising, in combination:
media movement actuator means in physical proximity to said inspection means for moving said unit under test to allow said inspection means to fully inspect said unit under test for defects; and
media movement driver means electrically coupled to said media movement actuator means and to said computer means for allowing said computer means to control said media movement actuator means by providing appropriate commands to said media movement driver means.

52. The method of claim 51 wherein said inspection means comprises surface inspection assembly means for inspecting at least one flat surface of said unit under test for defects while said media movement actuator means moves said unit under test.

53. The method of claim 52 wherein said inspection means further comprises edge inspection assembly means in physical proximity to said surface inspection assembly means for inspecting at least one edge of said unit under test for defects while said media movement actuator means moves said unit under test.

54. The method of claim 51 wherein said unit under test comprising a round disk having an outer edge and a hole in a center portion and wherein said media movement actuator means comprising at least one actuated roller and motor means for driving said actuated roller for turning said round disk.

55. The method of claim 54 wherein said media movement actuator means further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

56. The method of claim 55 wherein said actuated roller and said idler roller both having notch means in their circumferential faces in which said outer edge of said round disk is placed for permitting said round disk from slipping off said actuated roller and said idler roller during rotation.

57. The method of claim 51 wherein said unit under test comprising a rectangular flat panel and wherein said media movement actuator means comprising a lifter having a notch wherein an edge of said flat panel is placed and wherein said optical inspection assembly providing a linear sweep of a light beam on a flat surface of said flat panel, said lifter having a range of motion in a direction normal to a plane created by said linear sweep of said light beam, said lifter being coupled to and controlled by said computer means.

58. The method of claim 52 wherein said surface inspection assembly means comprising, in combination:
a light source providing said light beam;
optical scanner means having an aperture in physical proximity to said light source for permitting said light beam to contact said aperture on said optical scanner and for reflecting said light beam thereby providing a linear sweep of said light beam;
scanning optics means having a front face portion and a rear face portion for permitting said linear sweep of said light beam to contact said front face portion of said scanning optics means for causing said light beam that contacts said front face portion to exit said rear face portion and to contact said flat surface of said unit under test;
trigger detector means coupled to said computer means and placed within said linear sweep of said light beam for providing a synchronizing electrical signal to said computer means for indicating a position of said light beam along said linear sweep;
detection optics means having a front face portion and a rear face portion for permitting said light beam after contacting said unit under test to contact said rear face portion and exit said front face portion; and
said detector means for permitting said light beam exiting said front face portion of said detection optics means to be received by said detector means for detecting changes of a nominal Gaussian distribution of said light beam, said changes corresponding to and identifying defects in said flat surface of said unit under test.

59. The method of claim 58 wherein said optical scanner means having a motor-driven polygonal head coupled to said computer means and having reflective faces such that said light beam contacts said reflective faces of said polygonal head through said aperture, and having means for rotating said polygonal head for causing said light beam reflected off said reflective faces to create said linear sweep of said light beam across said scanning optics means.

60. The method of claim 59 wherein said motor-driven polygonal head is turned on and off by said computer means.

61. The method of claim 58 wherein said aperture of said optical scanner means being located at a distance from said scanning optics means equal to the focal length of said scanning optics means.

62. The method of claim 61 wherein said scanning optics means direct said light beam entering said front face portion such that said light beam exits said rear face in a direction normal to the focal plane of said scanning optics means.

63. The method of claim 58 wherein said scanning optics means focus said light beam on said flat surface of said unit under test.

64. The method of claim 58 wherein said trigger detector means comprising an optical sensor having an electrical output corresponding to the presence of said light beam on said optical sensor which is coupled to said computer means.

65. The method of claim 58 wherein said scanning optics means having a function as said detection optics means due to said light beam being projected by said scanning optics means to a reflective unit under test which reflects said light beam back to said scanning optics means.

66. The method of claim 58 wherein said detector means comprising, in combination:
at least two optical detectors having electrical outputs, said optical detectors functioning in parallel; and
electronic circuitry means for processing said electrical outputs of said optical detectors and generating an electrical signal to said computer means comprising, in combination:
first input means coupled to said electrical outputs of said optical detectors for monitoring said electrical outputs;
second input means coupled to said computer means for receiving a threshold value from said computer means;
processing means coupled to said first input means and to said second input means for measuring said electrical outputs of said optical detectors and for determining the existence of changes of said nominal Gaussian distribution of said light beam above said threshold value on said second input means; and output means coupled to said computer means for signaling an occurrence of a change above said threshold value to said computer means.

67. The method of claim 66 wherein said optical detectors are arranged in rows and columns to form a substantially square matrix.

68. The method of claim 66 wherein said optical detectors are arranged in a series of concentric circular rings.

69. The method of claim 51 further comprising the steps of:

loading said unit under test into said media movement actuator means in said optical inspection assembly;

activating said surface inspection assembly means with said computer means;

said computer means accessing said media movement driver, thereby causing said media movement actuator to move said unit under test such that the entirety of said flat surface is inspected;

checking with said computer means said output of said optical inspection assembly to determine whether a defect was detected by said optical inspection assembly; and unloading said unit under test from said optical inspection assembly into a first destination if said output on said optical inspection assembly did not indicate the presence of a defect on said unit under test, and unloading said unit under test from said optical inspection assembly into a second destination if said output of said optical inspection assembly did indicate the presence of a defect on said unit under test.

70. A method for detecting changes in a nominal Gaussian distribution of a light beam comprising the step of detecting changes in said nominal Gaussian distribution of said light beam, said detecting means comprising at least two optical detectors coupled together to function in parallel to detect changes in said nominal Gaussian distribution of said light beam.

71. An apparatus for optically scanning flat media comprising, in combination:

a light source providing a light beam;

light beam reflecting means for reflecting said light beam for providing a linear sweep of said light beam;

a unit under test having a flat surface to be inspected positioned in said linear sweep of said light beam;

detector means for receiving said light beam and for detecting changes of a nominal Gaussian distribution of said light beam corresponding to defects in said flat surface of said unit under test; and means for moving said unit under test within said linear sweep of said light beam and for permitting a linear scan of flat surface for complete scanning of all of said flat surface to be inspected.

72. The apparatus of claim 71 wherein said light source comprising a laser diode and said light beam comprising a laser beam from said laser diode.

73. The apparatus of claim 71 wherein said light source comprising a helium-neon laser, and said light beam comprising a laser beam from said helium-neon laser.

74. The apparatus of claim 71 wherein said light beam reflecting means comprising an optical scanner.

75. The apparatus of claim 74 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

76. The apparatus of claim 71 wherein said unit under test comprising a round disk having an outer edge and a hole in a center portion and wherein said means for moving said unit under test comprising at least one actuated roller and motor means for driving said actuated roller for turning said round disk.

77. The apparatus of claim 76 wherein said means for moving said unit under test further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

78. The apparatus of claim 77 wherein said actuated roller and said idler roller both having notch means in their circumferential faces in which said outer edge of said round disk is placed for preventing said round disk from slipping off said actuated roller and said idler roller during rotation.

79. The apparatus of claim 71 wherein said unit under test comprising a rectangular flat panel and wherein said means for moving said unit under test comprising a lifter having a notch wherein an edge of said flat panel is placed and wherein said optical inspection assembly providing a linear sweep of a light beam on a flat surface of said flat panel, said lifter having a range of motion in a direction normal to a plane created by said linear sweep of said light beam.

80. The apparatus of claim 71 wherein said detector means comprising, in combination:

at least two optical detectors having electrical outputs, said optical detectors functioning in parallel; and electronic circuitry means for processing said electrical outputs of said optical detectors and generating an electrical signal output in response to changes of a nominal Gaussian distribution of said light beam above a selectable threshold value.

81. A method for optically scanning flat media comprising, in combination:

providing a light source having a light beam;

providing light beam reflecting means for reflecting said light beam for providing a linear sweep of said light beam;

providing a unit under test having a flat surface to be inspected positioned in said linear sweep of said light beam;

providing detector means for receiving said light beam and for detecting changes of a nominal Gaussian distribution of said light beam corresponding to defects in said flat surface of said unit under test; and providing means for moving said unit under test within said linear sweep of said light beam and for permitting a linear scan of said flat surface for complete scanning of all of said flat surface to be inspected.

82. The method of claim 81 wherein said light beam reflecting means comprising an optical scanner.

83. The method of claim 82 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

84. The method of claim 81 wherein said unit under test comprising a round disk having an outer edge and a hole in a center portion and wherein said means for moving said unit under test comprising at least one actuated roller and motor means for driving said actuated roller for turning said round disk.

85. The method of claim 84 wherein said means for moving said unit under test further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

86. The method of claim 85 wherein said actuated roller and said idler roller both having notch means in their circumferential faces in which said outer edge of said round disk is placed for preventing said round disk from slipping off said actuated roller and said idler roller during rotation.

87. The method of claim 81 wherein said unit under test comprising a rectangular flat panel and wherein said means for moving said unit under test comprising a lifter having a notch wherein an edge of said flat panel is placed, said lifter having a range of motion in a direction normal to a plane created by said linear sweep of said light beam.

88. The method of claim 81 further comprising the steps of:
  placing said unit under test into said means for moving said unit under test; and
  activating said means for moving said unit under test causing all of said flat surface to pass through said linear sweep of said light beam.

89. An apparatus for detecting surface defects in flat media comprising, in combination:
  a light source providing a light beam;
  light beam reflecting means for reflecting said light beam for providing a linear sweep of said light beam;
  a unit under test having a flat surface to be inspected positioned in said linear sweep of said light beam;
  means for moving said unit under test within said linear sweep of said light beam and for permitting a linear scan of said flat surface for complete scanning of all of said flat surface to be inspected; and
  detector means for measuring changes in said light beam corresponding to defects on said flat surface of said unit under test, wherein said detector means receives said light beam and detects changes of a nominal Gaussian distribution of said light beam corresponding to defects in said flat surface of said unit under test.

90. The apparatus of claim 89 wherein said light source comprising a laser diode and said light beam comprising a laser beam from said laser diode.

91. The apparatus of claim 89 wherein said light source comprising a helium-neon laser, and said light beam comprising a laser beam from said helium-neon laser.

92. The apparatus of claim 89 wherein said light beam reflecting means comprising an optical scanner.

93. The apparatus of claim 92 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

94. The apparatus of claim 89 wherein said unit under test comprising a round disk having an outer edge and a hole in a center portion and wherein said means for moving said unit under test comprising at least one actuated roller and motor means for driving said actuated roller for turning said round disk.

95. The apparatus of claim 94 wherein said means for moving said unit under test further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

96. The apparatus of claim 95 wherein said actuated roller and said idler roller both having notch means in their circumferential faces in which said outer edge of said round disk is placed for preventing said round disk from slipping off said actuated roller and said idler roller during rotation.

97. The apparatus of claim 89 wherein said unit under test comprising a rectangular flat panel and wherein said means for moving said unit under test comprising a lifter having a notch wherein an edge of said flat panel is placed, said lifter having a range of motion in a direction normal to a plane created by said linear sweep of said light beam.

98. The apparatus of claim 89 wherein said detector means comprising, in combination:
  at least two optical detectors having electrical outputs, said optical detectors functioning in parallel; and
  electronic circuitry means for processing said electrical outputs of said optical detectors and generating an electrical signal output in response to changes of a nominal Gaussian distribution of said light beam above a selectable threshold value.

99. A method for detecting surface defects in flat media comprising, in combination:
  providing a light source having a light beam;
  providing light beam reflecting means for reflecting said light beam for providing a linear sweep of said light beam;
  providing a unit under test having a flat surface to be inspected positioned in said linear sweep of said light beam;
  providing means for moving said unit under test within said linear sweep of said light beam and for permitting a linear scan of said flat surface for complete scanning of all of said flat surface to be inspected; and
  providing detector means for measuring changes in said light beam corresponding to defects on said flat surface of said unit under test, wherein said detector means receives said light beam and detects changes of a nominal Gaussian distribution of said light beam corresponding to defects in said flat surface of said unit under test.

100. The method of claim 99 wherein said light beam reflecting means comprising an optical scanner.

101. The method of claim 100 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

102. The method of claim 99 wherein said unit under test comprising a round disk having an outer edge and a hole in a center portion and wherein said means for moving said unit under test comprising at least one actuated roller and motor means for driving said actuated roller for turning said round disk.

103. The method of claim 102 wherein said means for moving said unit under test further comprising at least one idler roller, said idler roller and said actuated roller contact said outer edge of said round disk, said actuated roller rotating in response to said motor means driving said actuated roller, causing rotation of said round disk, said rotation of said disk causing said idler roller to rotate.

104. The method of claim 103 wherein said actuated roller and said idler roller both having notch means in their circumferential faces in which said outer edge of said round disk is placed for preventing said round disk from slipping off said actuated roller and said idler roller during rotation.

105. The method of claim 99 wherein said unit under test comprising a rectangular flat panel and wherein said means for moving said unit under test comprising a lifter having a notch wherein an edge of said flat panel is placed, said lifter having a range of motion in a direction normal to a plane created by said linear sweep of said light beam.

106. The method of claim 99 wherein said detector means comprising, in combination:

at least two optical detectors having electrical outputs, said optical detectors functioning in parallel; and electronic circuitry means for processing said electrical outputs of said optical detectors and generating an electrical signal output in response to changes of a nominal Gaussian distribution of said light beam above a selectable threshold value.

107. The method of claim 99 further comprising the steps of:

placing said unit under test into said means for moving said unit under test;

activating said means for moving said unit under test causing all of said flat surface to pass through said linear sweep of said light beam; and activating said detector means.

* * * * *